US009918679B2

(12) United States Patent
Janata et al.

(10) Patent No.: US 9,918,679 B2
(45) Date of Patent: Mar. 20, 2018

(54) SONIFICATION SYSTEMS AND METHODS FOR AUDITORY DISPLAY OF PHYSIOLOGICAL PARAMETERS

(71) Applicants: THE REGENTS OF THE UNIVERSITY OF CALIFORNIA, Oakland, CA (US); NEW TECHNOLOGY SOUNDINGS, LLC, Hanover, NH (US); TRUSTEES OF DARTMOUTH COLLEGE, Hanover, NH (US)

(72) Inventors: Petr Janata, Davis, CA (US); Beau Sievers, Brooklyn, NY (US); William H. Edwards, Norwich, VT (US)

(73) Assignees: THE REGENTS OF THE UNIVERSITY OF CALIFORNIA, Oakland, CA (US); NEW TECHNOLOGY SOUNDINGS, LLC, Hanover, NH (US); TRUSTEES OF DARTMOUTH COLLEGE, Hanover, NH (US)

( * ) Notice: Subject to any disclaimer, the term of this patent is extended or adjusted under 35 U.S.C. 154(b) by 625 days.

(21) Appl. No.: 14/549,388

(22) Filed: Nov. 20, 2014

(65) Prior Publication Data
US 2015/0133749 A1 May 14, 2015

Related U.S. Application Data

(63) Continuation of application No. PCT/US2013/043184, filed on May 29, 2013.
(Continued)

(51) Int. Cl.
*G08B 1/08* (2006.01)
*A61B 5/00* (2006.01)
(Continued)

(52) U.S. Cl.
CPC ............ *A61B 5/7415* (2013.01); *A61B 5/024* (2013.01); *A61B 5/0205* (2013.01);
(Continued)

(58) Field of Classification Search
CPC .......... A61B 5/7415; A61B 5/00; G06F 19/00
(Continued)

(56) References Cited

U.S. PATENT DOCUMENTS 7,070,570 B2 * 7/2006 Sanderson ........... A61B 5/0836
422/84
7,338,410 B2 3/2008 Dardik, III
(Continued)

FOREIGN PATENT DOCUMENTS

WO 2008-135329 A1 11/2008

OTHER PUBLICATIONS

ISA/US, United States Patent and Trademark Office, International Search Report and Written Opinion dated Oct. 24, 2013, pp. 1-16, with claims searched, pp. 17-23.

*Primary Examiner* — Toan N Pham
(74) *Attorney, Agent, or Firm* — O'Banion & Ritchey LLP; John P. O'Banion

(57) ABSTRACT

Systems and methods for generating a sonification output for presenting information about physiological parameters such as oxygen saturation and heart rate parameters in discrete auditory events. In a preferred embodiment, each event comprises two sounds. The first is a reference sound that indicates the desired target state for the two parameters and the second indicates the actual state. Heart rate is preferably represented by amplitude modulation. Oxygen saturation is preferably represented by a timbral manipulation.

30 Claims, 35 Drawing Sheets

Related U.S. Application Data

(60) Provisional application No. 61/652,679, filed on May 29, 2012.

(51) Int. Cl.
 *A61B 5/024* (2006.01)
 *A61B 5/145* (2006.01)
 *A61B 5/0205* (2006.01)
 *A61B 5/1455* (2006.01)

(52) U.S. Cl.
 CPC ...... *A61B 5/14542* (2013.01); *A61B 5/14551* (2013.01); *A61B 5/7282* (2013.01); *A61B 5/746* (2013.01); *A61B 5/02416* (2013.01)

(58) Field of Classification Search
 USPC .................. 340/539.12, 568.1, 568.2, 573.1
 See application file for complete search history.

(56) References Cited

U.S. PATENT DOCUMENTS

| | | |
|---|---|---|
| 7,643,881 B2 | 1/2010 | Armstrong |
| 8,095,192 B2 * | 1/2012 | Baker, Jr. ............... A61B 5/024 600/310 |
| 2004/0193026 A1 | 9/2004 | Scharf |
| 2005/0096512 A1 | 5/2005 | Fox et al. |
| 2006/0111621 A1 | 5/2006 | Coppi et al. |
| 2009/0223318 A1 | 9/2009 | Lemons |

* cited by examiner

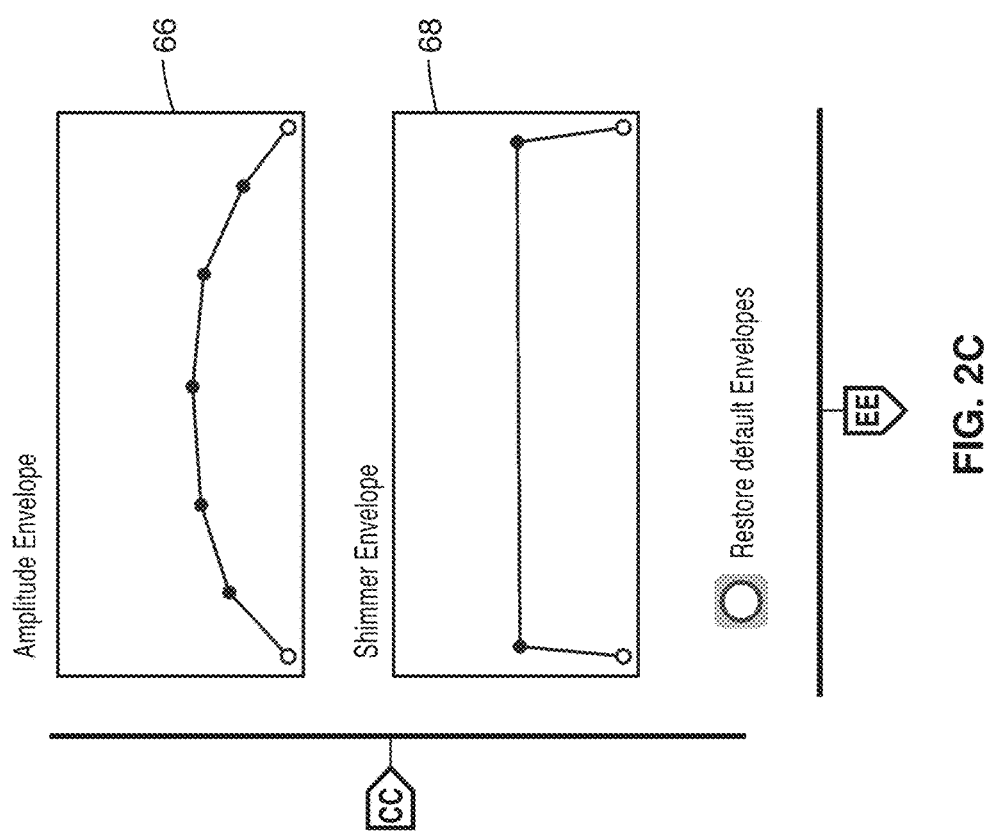

1, StepTest_PJ_1;
2, OxygenSat HeartRate;
3, 50.0000 40.0000 ;
4, 80.0000 40.0000 ;
5, 90.0000 40.0000 ;
6, 96.0000 40.0000 ;
7, 100.0000 40.0000 ;
8, 50.0000 90.0000 ;
9, 80.0000 90.0000 ;
10, 90.0000 90.0000 ;
11, 96.0000 90.0000 ;
12, 100.0000 90.0000 ;
13, 50.0000 140.0000 ;
14, 80.0000 140.0000 ;
15, 90.0000 140.0000 ;
16, 96.0000 140.0000 ;
17, 100.0000 140.0000 ;
18, 50.0000 190.0000 ;
19, 80.0000 190.0000 ;
20, 90.0000 190.0000 ;
21, 96.0000 190.0000 ;
22, 100.0000 190.0000 ;
23, 50.0000 230.0000 ;
24, 80.0000 230.0000 ;
25, 90.0000 230.0000 ;
26, 96.0000 230.0000 ;
27, 100.0000 230.0000 ;
28, 100.0000 230.0000 ;

300 # SONIFICATION SYSTEMS AND METHODS FOR AUDITORY DISPLAY OF PHYSIOLOGICAL PARAMETERS

CROSS-REFERENCE TO RELATED APPLICATIONS

This application is a 35 U.S.C. § 111(a) continuation of PCT international application number PCT/US2013/043184 filed on May 29, 2013, incorporated herein by reference in its entirety, which claims priority to, and the benefit of, U.S. provisional patent application Ser. No. 61/652,679 filed on May 29, 2012, incorporated herein by reference in its entirety. Priority is claimed to each of the foregoing applications.

The above-referenced PCT international application was published as PCT International Publication No. WO 2014/007927 on Jan. 9, 2014, which publication is incorporated herein by reference in its entirety.

STATEMENT REGARDING FEDERALLY SPONSORED RESEARCH OR DEVELOPMENT

Not Applicable

INCORPORATION-BY-REFERENCE OF MATERIAL SUBMITTED IN A COMPUTER PROGRAM APPENDIX

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

1. Technical Field

This technology pertains generally to sonification systems and methods, and more particularly to sonification systems and methods for auditory display of physiological parameters during patient monitoring.

2. Background Discussion

Clinical settings requiring simultaneous monitoring of time-varying fluctuations in multiple physiologic parameters present a challenge for clinical staff who must make therapeutic decisions based on changes in these parameters. Although most monitoring devices sound auditory alarms when values of physiologic parameters cross preset thresholds, such alarms are often limited in utility, in large part because the number of false alarms is so high that the alarms are ignored. Often, they also continue sounding when parameter values have returned to a normal range, thus requiring staff to interrupt current tasks in order to turn the alarm off. Importantly, alarms associated with different physiologic parameters are rarely integrated into a coherent information stream. These various considerations have led to a general dissatisfaction with the state of auditory display in clinical settings and calls for improvement of medical information displays.

Part of the challenge in altering the soundscape of clinical settings is to make the auditory information more informative. One attempt to do so is represented by the IEC 60601-1-8 melodic alarm standard in which different monitored parameters are associated with specific melodies. Despite the appeal of such an idea, testing of the ability to learn and discriminate what alarm conditions the different melodies signify has shown this standard to be unusable, prompting some to call for a revision of the standard.

Although it is important to maintain monitored physiologic parameters within acceptable ranges, in many clinical settings, the need for particular attention to this issue in neonatal intensive care patients is becoming increasingly apparent. For example, oxygen saturation targeting has become an important strategy to decrease morbidity from over- or under-oxygenation. Excessively high oxygen saturation is associated with retinopathy of prematurity, while low levels of saturation are concerning for potential risks of inadequate oxygen delivery to developing tissues. While maintaining oxygen saturation within target goals is desirable, it remains challenging to achieve in the clinical setting. It has been demonstrated that actual oxygen saturation levels often exceed the desired ranges, with more of a predilection for excessive levels.

Delivery room stabilization of extremely preterm infants presents another challenge. Providers are faced with new recommendations to achieve a changing target of oxygen saturation while simultaneously performing other stabilizing interventions. Current monitoring strategies focus on visual display of data and alarms when thresholds are exceeded. The noise of alarms themselves may have destabilizing effects on the fragile stability of vulnerable sick neonates, while giving little opportunity to make adjustments to prevent alarm conditions.

BRIEF SUMMARY

With the various considerations raised above in mind, an objective of the technology described herein is a sonification system aimed at compactly representing information about physiological parameters such as heart rate and oxygen saturation.

Maintaining physiologic parameters such as oxygen saturation within desired ranges is challenging in many clinical situations. High rates of false positive alarms in clinical settings limit the utility of the alarms that trigger when thresholds are exceeded. Auditory displays incorporating the semantic connotations of sounds and the processing limitations of human perception and cognition may improve monitoring.

By shifting from a reliance on pitch to indicate changes on a physiologic dimension that is not inherently associated with pitch, we hope to reduce the perceptual and cognitive demands associated with mapping specific pitches to specific oxygen saturation levels, and reduce perceptual interference with other tone emitting monitoring equipment.

The described sonification methods may effectively communicate information about current heart rate and oxygen saturation status relative to desired target levels. Clinical monitoring settings are identified in which a stream of discrete auditory informational items may be useful.

Though motivated by the specific needs of neonatal intensive care settings, the principles of the sonification we develop here are applicable for a variety of clinical settings and physiologic variables.

Further aspects of the technology will be identified in the following portions of the specification, wherein the detailed description is for the purpose of fully disclosing preferred embodiments of the technology without placing limitations thereon.

BRIEF DESCRIPTION OF THE SEVERAL VIEWS OF THE DRAWING(S)

The technology will be more fully understood by reference to the following drawings which are for illustrative purposes only:

FIG. 2A through FIG. 2E show detailed expanded views of the computer-generated front panel of FIG. 2.

FIG. 14A through FIG. 14F show time-frequency plots of six of the component sounds that were used in the sonifications of the technology described herein. In the column on the left there is only 1 cycle of amplitude modulation (AM), signifying a heart rate (HR) level of z=−2, while in the right column there are 3 cycles of AM denoting a HR level of z=0. Variation across rows represents changes in the oxygen saturation ($O_2$Sat) parameter. Starting with a pure tone in the bottom row that denotes a desaturated state, increasing levels of oxygen saturation are represented by increased energy in higher frequencies. This rise in spectral centroid increases the perceived brightness of the sound.

Figure 15:
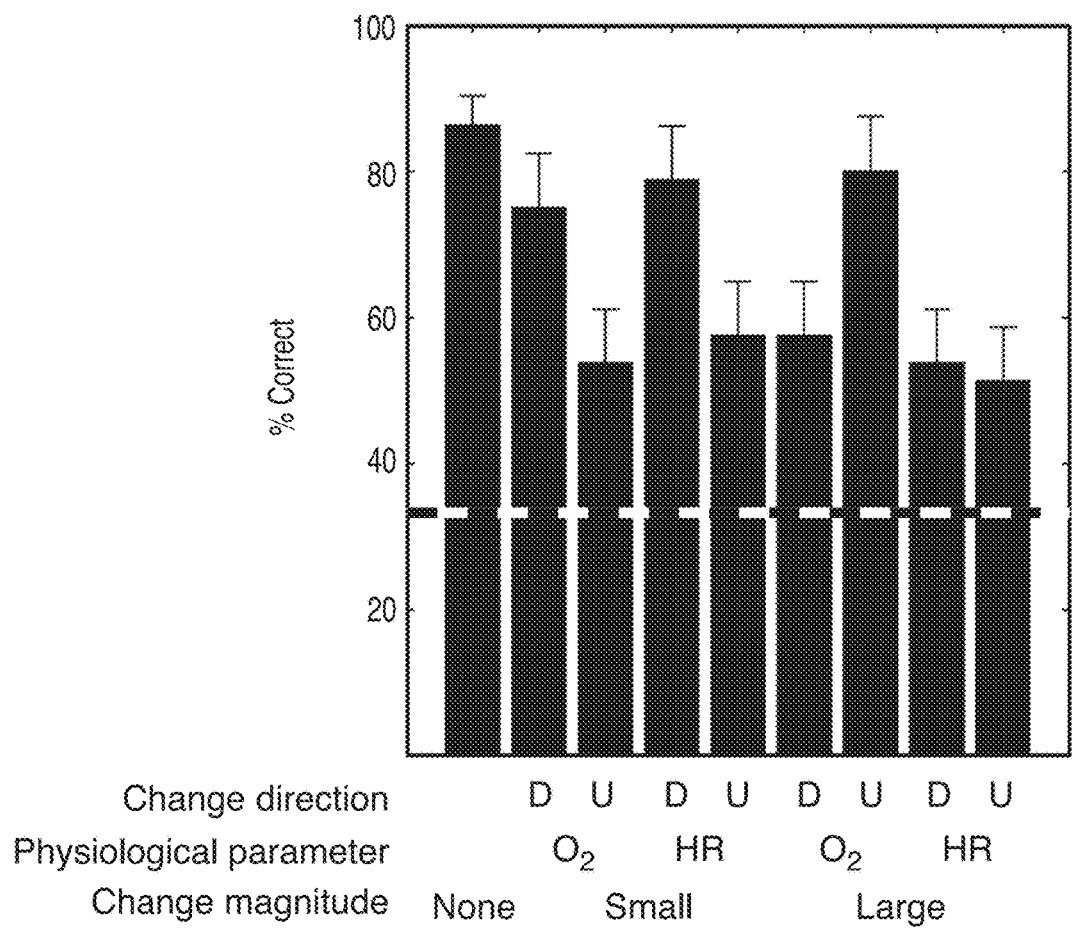

FIG. 15 is a plot of average performance on the change magnitude task, separated by the degree of change (None, Small, Large), the signified physiologic parameters of oxygen saturation ($O_2$) and heart rate (HR), and downward (D) and upward (U) direction of change. The dashed line indicates chance performance. Error bars represent 1 standard error of the mean.

Figure 16:
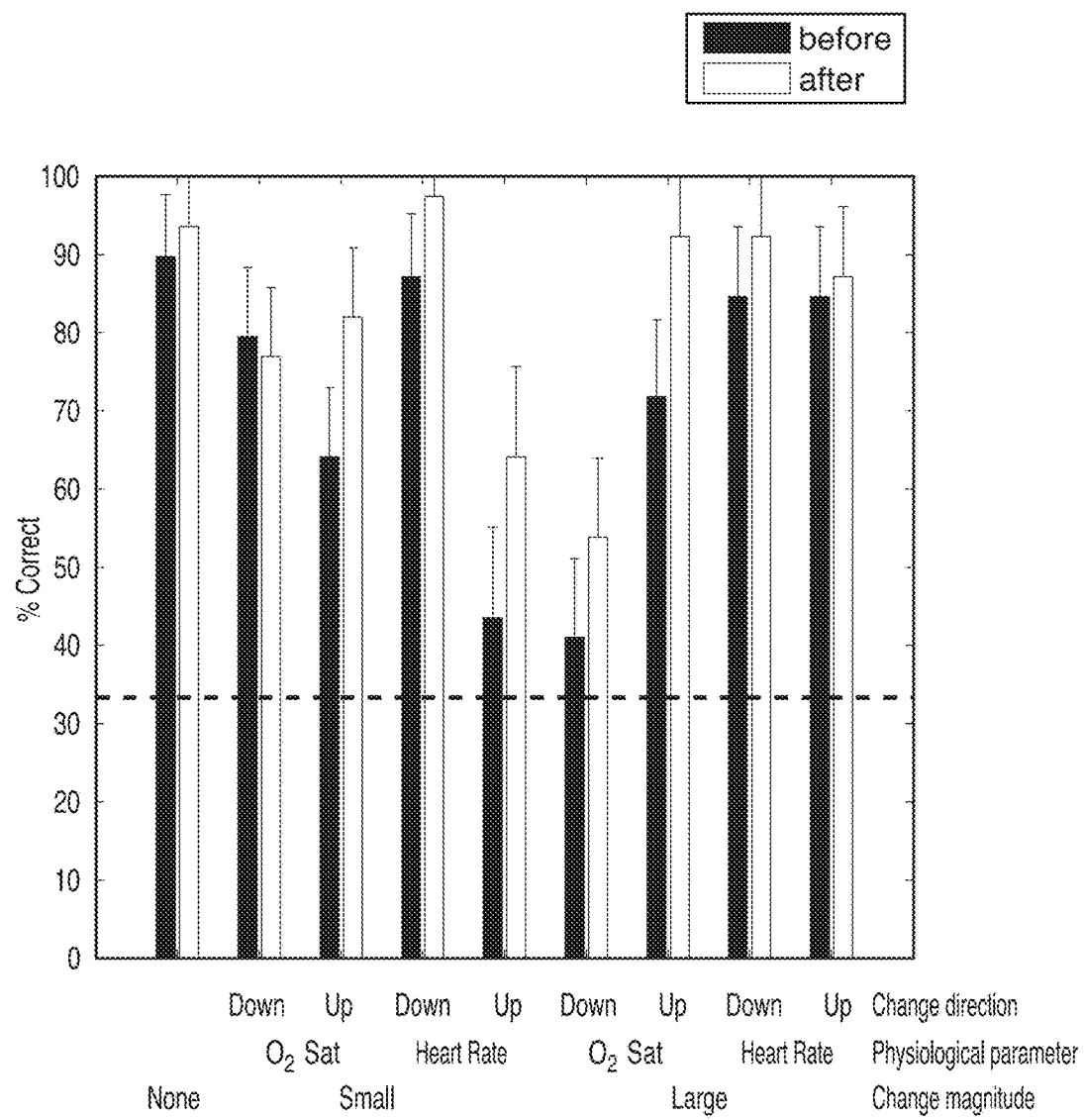

FIG. 16 is a plot showing the effect of training on change magnitude task performance, separated by the type of change trial. Dark bars indicate initial performance without feedback, and light bars indicate performance on the last three trials within each category following training to a performance criterion of 87.5% (averaged across categories). The dashed line indicates chance performance. Error bars represent 1 standard error of the mean.

DETAILED DESCRIPTION

The technology described herein provides a sonification system and method to convey deviations in heart rate and oxygen saturation from a desired target level.

Figure 1:
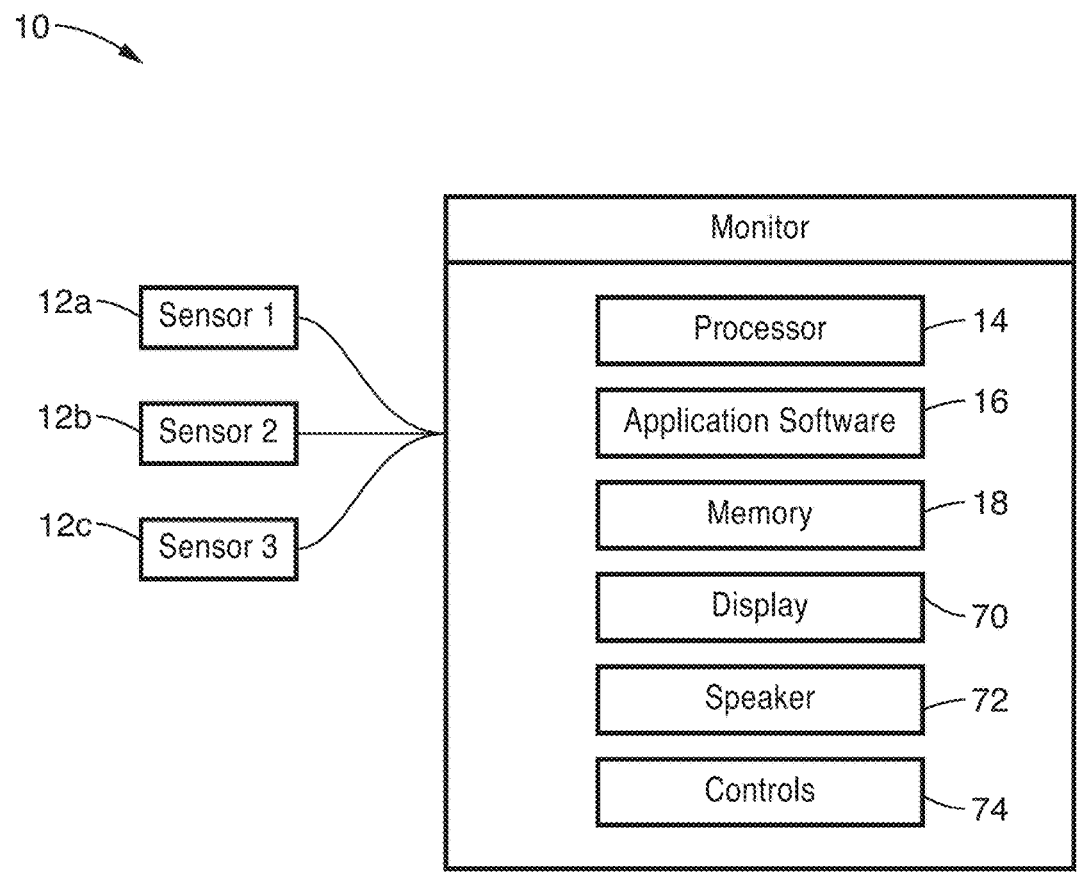
FIG. 1 shows a schematic diagram of a patient monitoring system using the sonification scheme of the technology described herein.

FIG. 1 illustrates a schematic diagram of a monitoring system 10 incorporating the sonification methods of the technology described herein to provide auditory display of one or more physiological parameters while monitoring a patient.

System 10 includes a plurality of sensors 12a, 12b, 12c that are coupled to the patient to individually provide real-time data relating to physiological parameters of the patent. In an exemplary monitoring scenario, sensors 12a, 12b, 12c may comprise a pulse oximeter providing oxygen saturation data, a heart rate monitor providing heart rate data, and a respiratory monitor providing respiratory rate data. It is appreciated that a lesser or greater number of sensors, and corresponding physiological parameters, may be used for the monitoring system and sonification of parameters.

While the bulk of the specific features of the sonification system and methods of the technology described herein are generally contained within the application software 16, it is appreciated that a monitoring system 10 will often require some integration of the sonification features with other components of the monitor. For example, the sonification system embodied in application software 16 will generally receive as input the same data generated for display of the physiological parameters (e.g. heart rate and oxygen saturation) on the display 70. The monitoring system 10 includes a processor 14 for executing application software 16, as well as memory 18 for storing the software 16 and any data relating to preferences or setup associated with the software 16. Auditory signals that are generated from application software 16 are delivered through one or more speakers 72 coupled to the monitor 10. In addition, controls 74 (e.g. touch screen, buttons, keyboard, mouse, etc.) are provided for input of preferences and options relating to application software 16.

Application software 16 is configured to input sensor data 200 (see FIG. 6, and method 600 of FIG. 13) and generate a sonification output of a physiological parameter's desired target level and deviations according to one or more preset acoustic parameters. As described below in further detail, acoustic parameters are selected individually for each physiological parameter being monitored, and in particular with regard to which acoustic parameter's changes would map to appropriate connotations of changes in the corresponding heart rate and oxygen saturation.

In a preferred embodiment, the sonification for semantic mapping is discrete, with each acoustic instance conveying information about a desired target state and the current deviation from that state. Recognizing the difficulties inherent in making subtle discriminations in absolute values of acoustic parameters, parameter changes are configured such that they would create a small set (e.g. two) of levels below and a small set (e.g. two) of levels above the target state for each dimension, with the idea that transition points could be mapped to arbitrary deviations from the target, homeostatic, state according to the specific requirements of any given clinical scenario. This is based on the premise that a small set of mappings between physiological deviation levels and acoustic changes will be easier to learn and utilize than a continuous mapping between absolute values of physiologic and acoustic variables.

Thus, sonifications described herein are based on the standardized scores (e.g. z-scores) to convey the amount of deviation of a physiological signal from a desired target level using a small number of levels of variation, which we refer to as standard deviation units (SDUs).

Accordingly, sonification for each physiological parameter will preferably have 5 levels, or deviations, associated with various threshold (target, or homeostatic ($z=0$), first threshold above ($z=+1$), second threshold above ($z=+2$), first threshold below ($z=-1$), and second threshold below ($z=-2$). It is appreciated that these 5 levels may vary according to clinical situation or environment. For example, neonatal intensive care delivery may have a set acoustical parameter for the target state (0), whereas for a nursery setting, the acoustical parameter for the target state (0) may not have any sonification output whatsoever (e.g. silence).

Acoustic attributes assigned to specific states may vary by one or more variables, e.g. duration, frequency, amplitude, shimmer, mod rate, etc. Selection and variation of acoustic attributes are configured to be inherently evocative of the physiological variable being represented, with variation along the attribute spanning a range of values that are both discriminable and evocative of abnormal or dangerous states at either end, i.e. $|z|=2$. Generally, the sound representing $z=0$ is selected to be neutral or slightly pleasing when listened to repeatedly.

Stimuli preferably comprise of a pair of sounds, in which the first sound represents the reference ($z=0$ along both dimensions) against which any deviation in the second sound could be judged.

In one embodiment, heart rate is represented by the rate of amplitude modulation (AM) of the sound. AM is one of the most discernible and discriminable forms of temporal modulation, and is semantically congruous with representing heart rate, which we often perceive when we hear or feel our heart beat. The SDU level of $z=0$ is represented by three cycles within the 500 ms period (6 Hz). Each increasing or decreasing step in z was associated with the addition or subtraction of 1 cycle, respectively. Thus, variation in represented heart rate was associated with changes in the amount of flutter of the sound.

Oxygen is a more challenging variable for which to establish a semantic mapping. Although variation in pitch is commonly used in oxygen monitors to represent oxygen saturation, there is nothing inherent in pitch change that evokes the concept of changing oxygen saturation. Thus, we chose to represent oxygen saturation by the timbre of the sound. Because oxygen is a gas, it is readily associated with the concept of effervescence. Thus, we sought to identify sound synthesis control parameters that could manipulate the perceived sense of effervescence between a desaturated state and a dangerously saturated state, while not changing the sound so much that it would be perceived as manipulation of an entirely different physiologic variable.

FM synthesis was used for this purpose. In FM synthesis, a carrier frequency is modulated with a second frequency of some amplitude. The ratio of the modulator frequency to the carrier frequency determines which additional frequencies (partials) are added to the sound and whether the resulting complex harmonic sound is consonant or dissonant. In addition, the amplitude of the modulating frequency influences the relative amplitudes of the partials and therefore the brightness of the sound. At one extreme, only the carrier frequency is present as a pure tone. This pure tone was used to represent complete desaturation ($z=-2$). For $z=+2$ we chose a modulator frequency twice that of the carrier frequency and a time-varying amplitude envelope such that the sound had a somewhat displeasing shimmer to it, intending to evoke perception of a dangerously saturated condition. Note that increasing the number of harmonics and/or manipulating their relationships tended to lead to increases in the sense of urgency.

Hardware and Software Implementation

Figure 2:
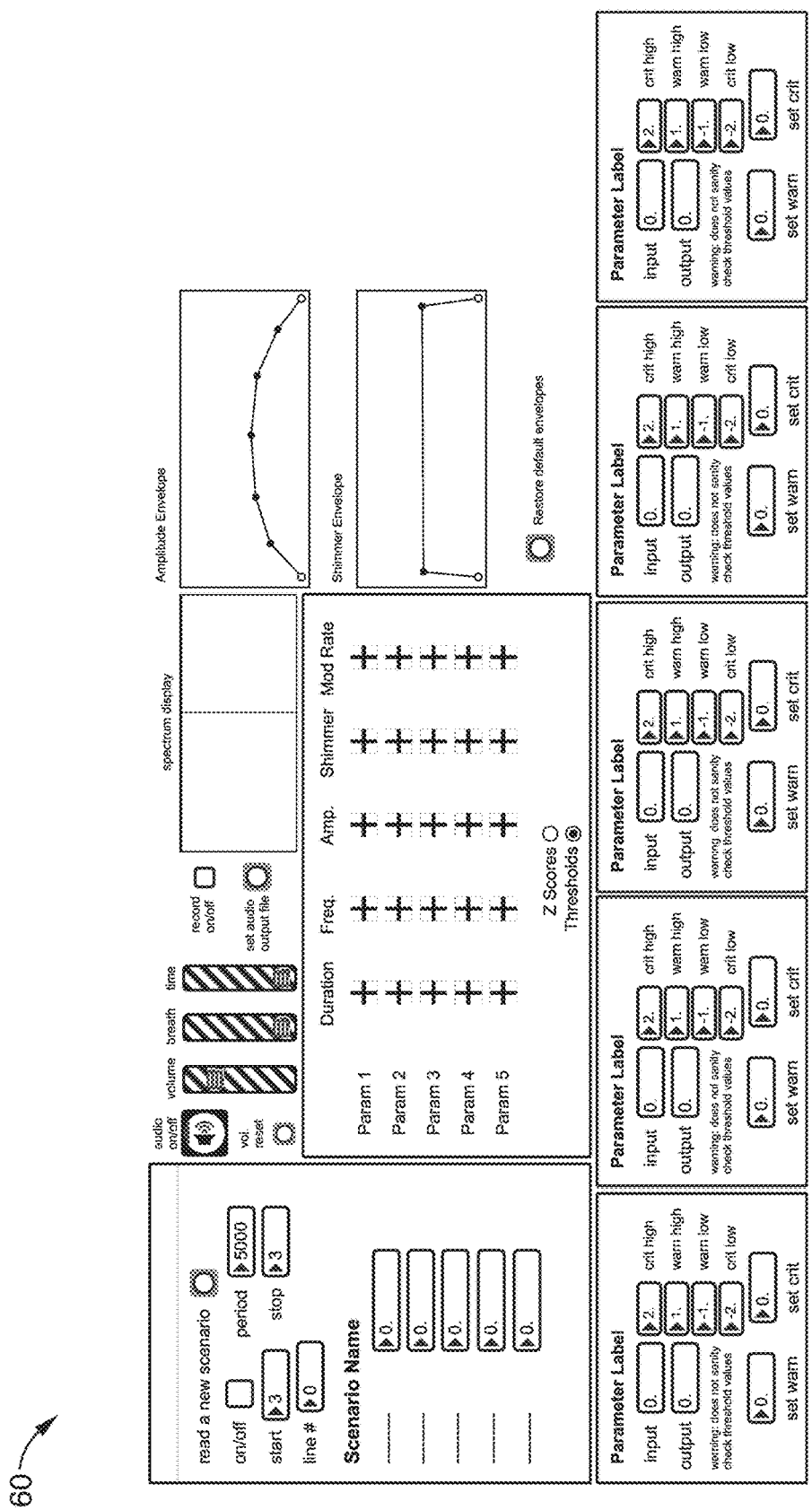
FIG. 2 illustrates a screen view of a computer-generated front panel of a user interface of an exemplary computer-based system for implementation of the sonification methods of the technology described herein.

FIG. 2 illustrates an example of a computer generated front panel 60 of a user interface in accordance with the technology described herein. In this embodiment (illustrated in FIG. 2 through FIG. 12), the Max visual programming language (from Cycling '74, Walnut, Calif.) for real-time manipulation and synthesis of sound was used. It is appreciated, however, that the sonification method of the technology described herein may be encoded using a number of different platforms available in the art. Max/MSP patches provide programming information/algorithms that cause the Max software to generate sonification according to the technology described herein. The Max software can run on a general purpose computer that would be connected to sensors 12a, 12b, 12c on the patient or other subject.

Figure 2A:
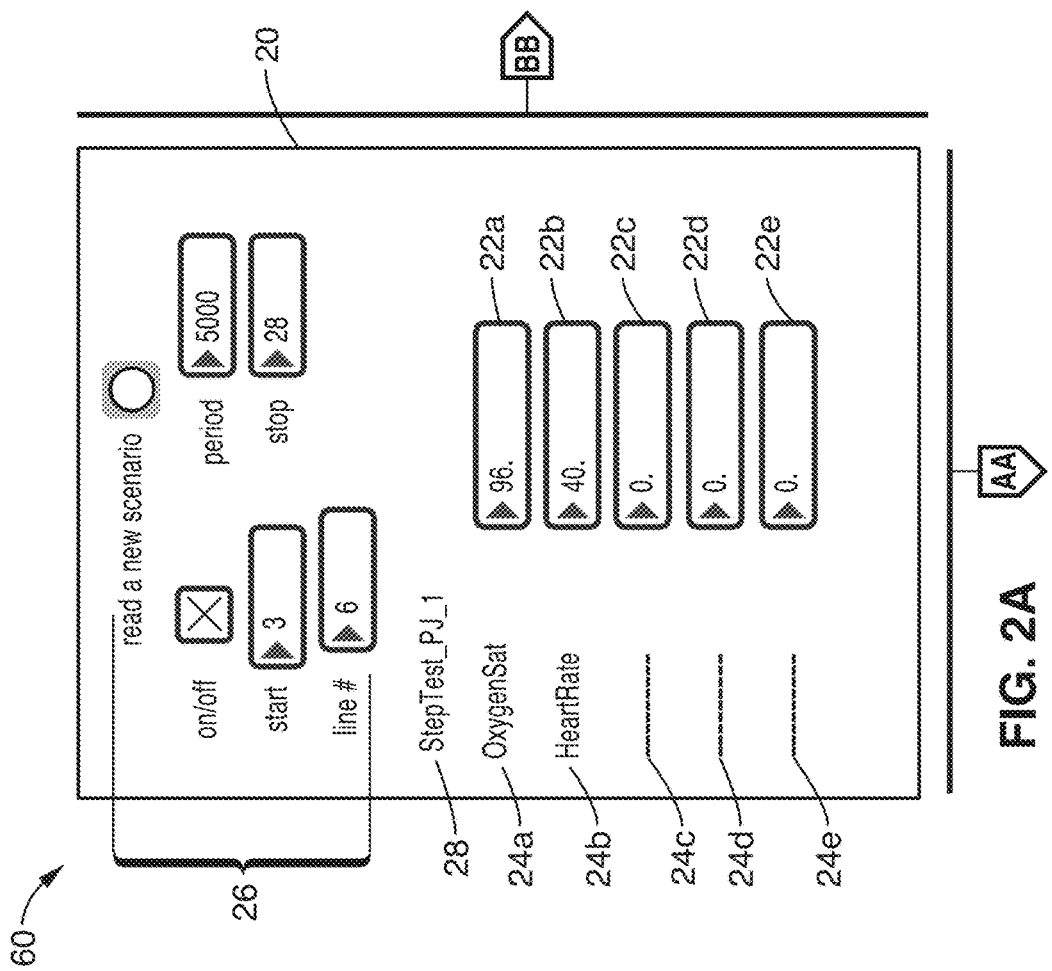

Shown at the top left of FIG. 2 and in the expanded view of FIG. 2A is the module/patch "new_data_reader" 20 for specifying the input data stream "scenario" 28, in this case with a name 28 of "StepTest_PJ_1." The scenario type 28 may be specific to patient or clinical setting. The physiological variable identifiers 24a-24e are read from the data stream 200 (FIG. 6) and dynamically populate the remainder of the interface. Also shown are the current parameter values 22a-24e, e.g. OxygenSat and HeartRate values of 96% and 40 beats per minute, respectively. With fields 26, the reader 20 can specify where in the data stream 200 to start and stop, etc.

Figure 2B:
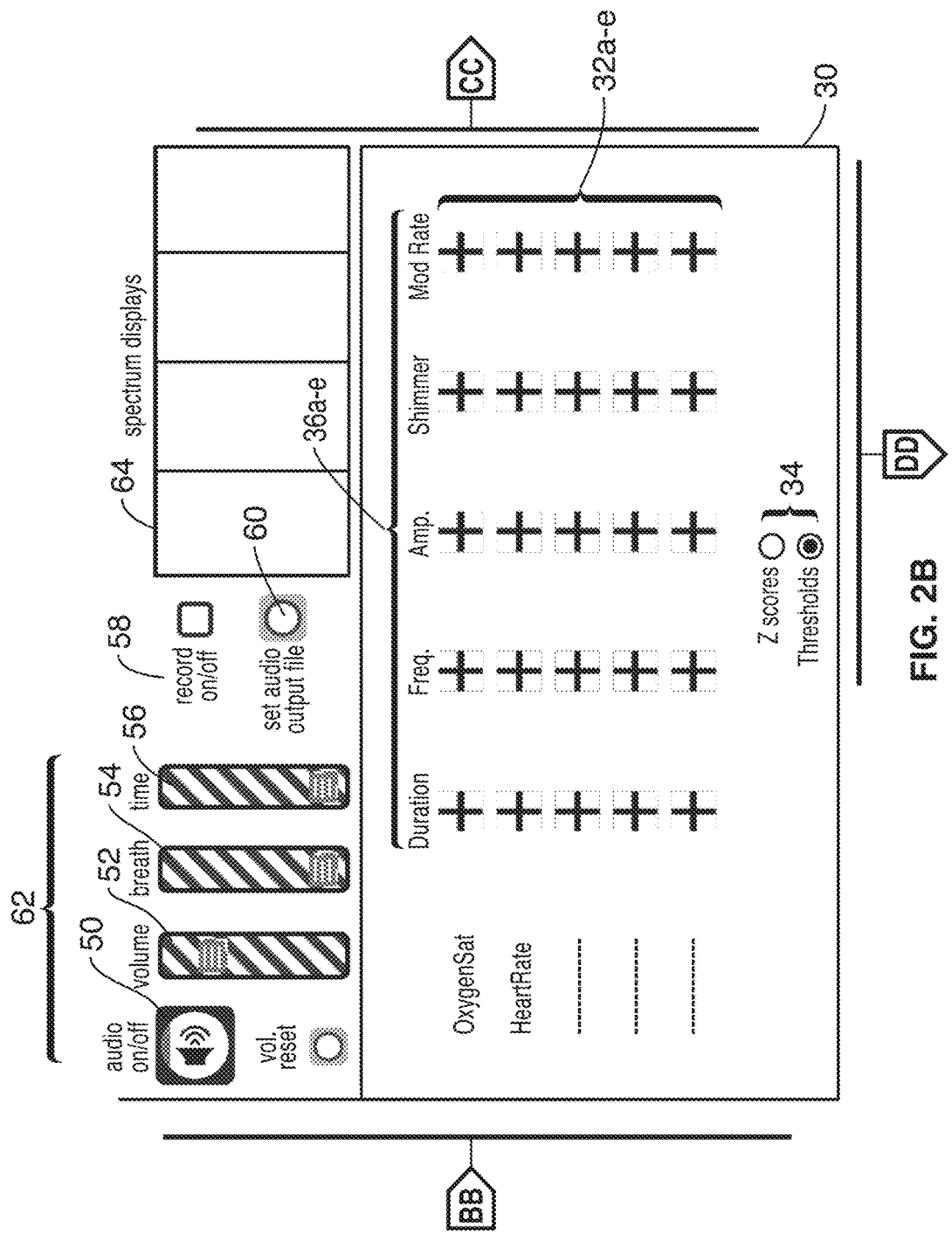

The matrix of crosses in the panel in the middle of FIG. 2, which are shown in greater detail in FIG. 2B, shows the "dynamic router" interface 30 for mapping physiological variables 32a-32e to acoustic variables 36a-36e. As shown in FIG. 2B, interface 30 includes fields for up to 5 physiological variables 32a-32e (with two showing actual data input (Oxygen Sat 32a and Heartrate 32b) and 5 acoustic variables 36a-36e (duration 36a, frequency (pitch) 36b, amplitude 36c, shimmer 36d and modification rate 36e (e.g. 1/s). The black dots indicate that OxygenSat 32a is presently mapped to the timbral variation 36d, "Shimmer," and HeartRate 32b is presently mapped to the rate of amplitude modulation 36e, "Mod Rate." As explained above, the "shimmer" variable may elicit an "effervescence" to the output sound signal, with higher shimmer giving a brighter, more metallic feel, and lower shimmer being more flute-like. Also shown in FIG. 2B are a series of controls 62 (e.g.

toggles for volume 52, breathing 54, time 56, mute 50, recording 58, and output audio file recording 60). A spectrum display 64 is also provided.

Referring to the detailed view of FIG. 2C, the user may modify the shape of the amplitude envelope 66 and shimmer envelope 68 according to desired preferences.

Figure 2D:
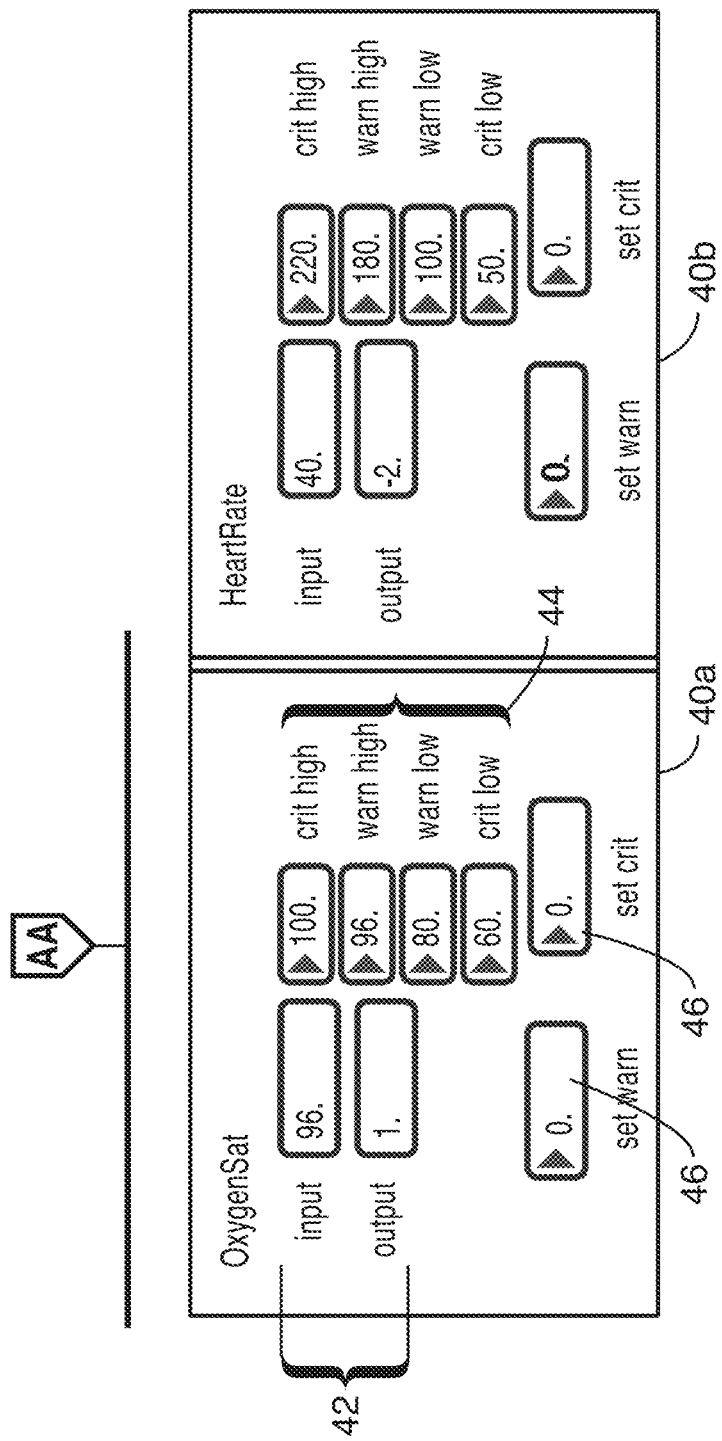
Figure 2E:
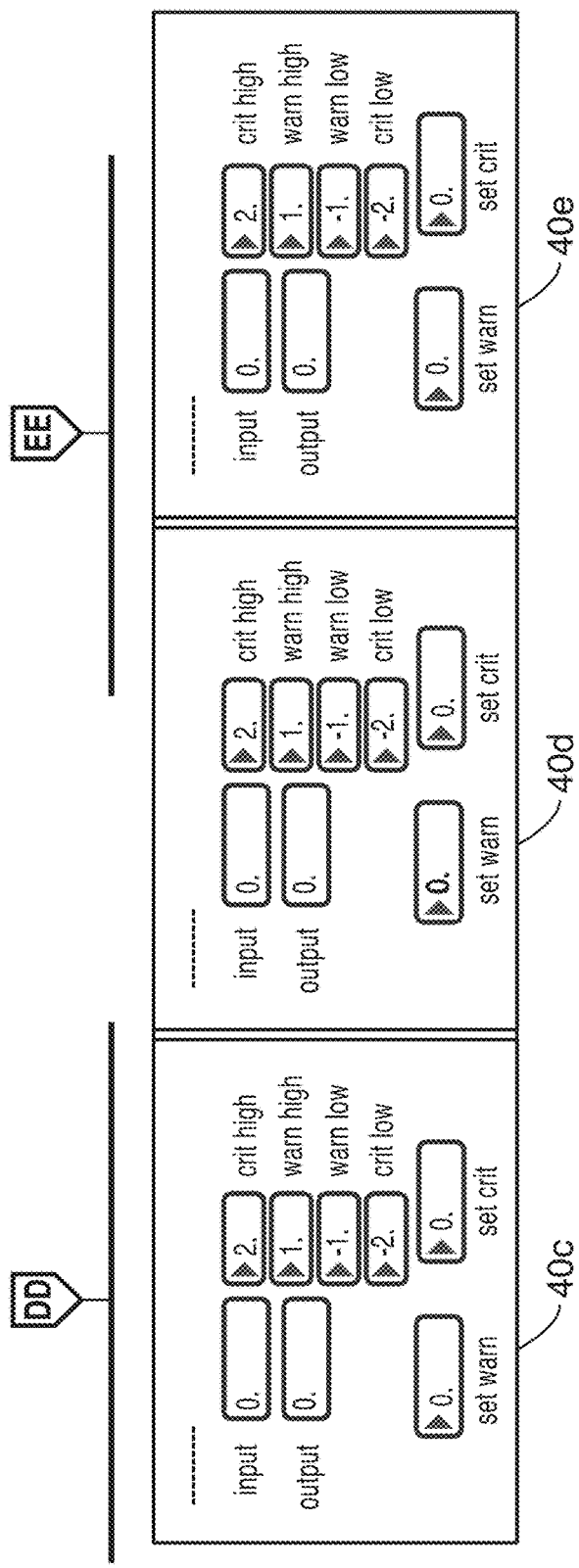

Along the bottom of FIG. 2, and shown in greater detail in the expanded views of FIG. 2D and FIG. 2E, is an array of "dynamic discretizer" modules 40*a* (OxygenSat), 40*b* (HeartRate), 40*c* (empty), 40*d* (empty), and 40*e* (empty), in which the input value is transformed to an output value (illustrated in fields 42) designating one of the five output categories Z-scores {−2=crit low, −1=warn low, 0=target, 1=warn high, 2=crit high}. The four thresholds 44 are shown for triggering the boundaries of each of the five ranges. The categories can be based, for example, either on z-scores or thresholds per toggle 34 in FIG. 2B (output 42 OxygenSat is shown as a having a z-score of 1, based on the input of 96 (right at the "warn high" threshold). Shown here are thresholds 44 for transforming OxygenSat and HeartRate values into the discrete categories 40*a* and 40*b*. Each module has input fields 46 for allowing user modification of the ranges.

Figure 3A:
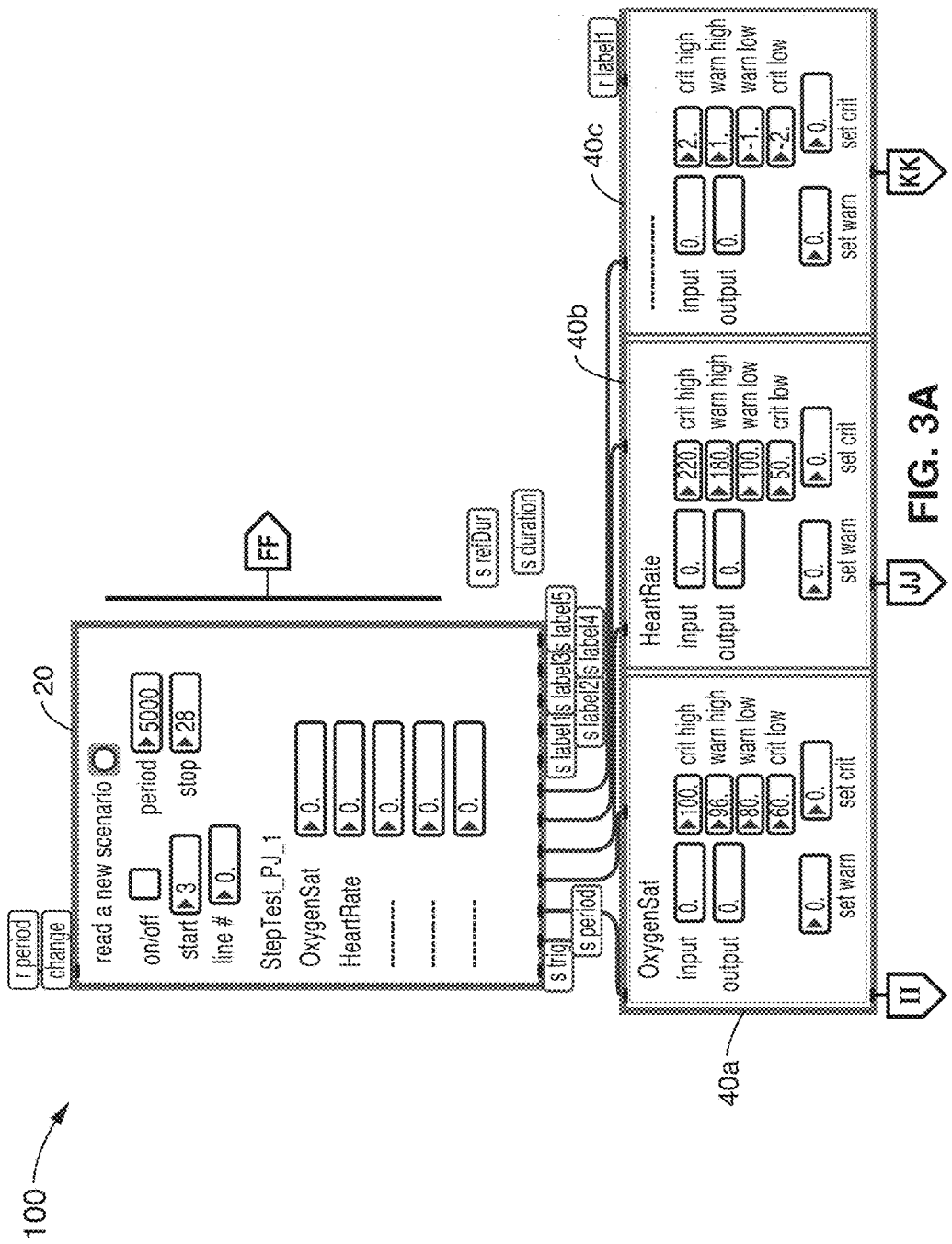
FIG. 3A through FIG. 3H illustrate a flow diagram of a software patch designating interrelationships between the individual modules underlying the front panel shown in FIG. 2.
Figure 3B:
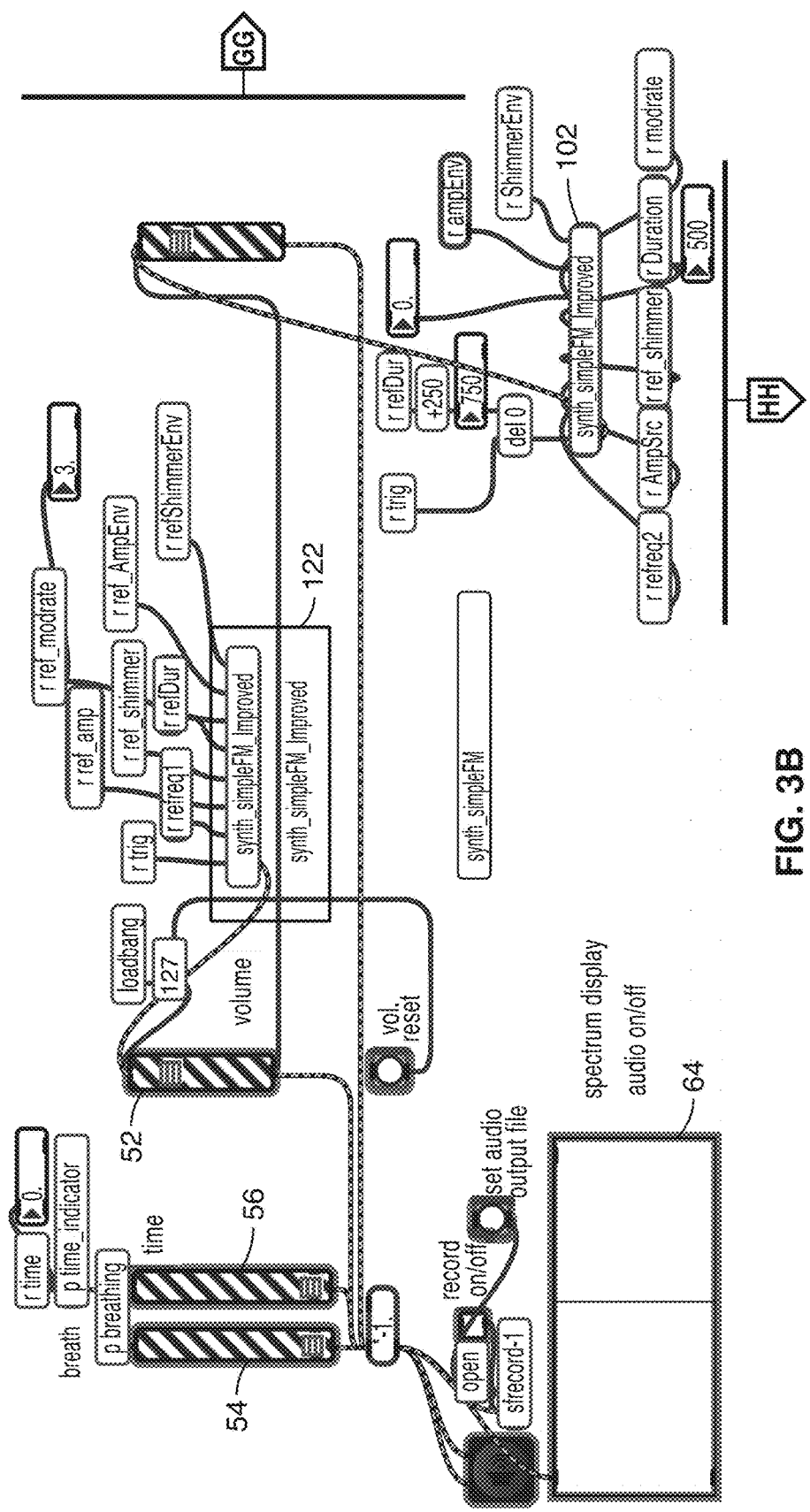
Figure 3C:
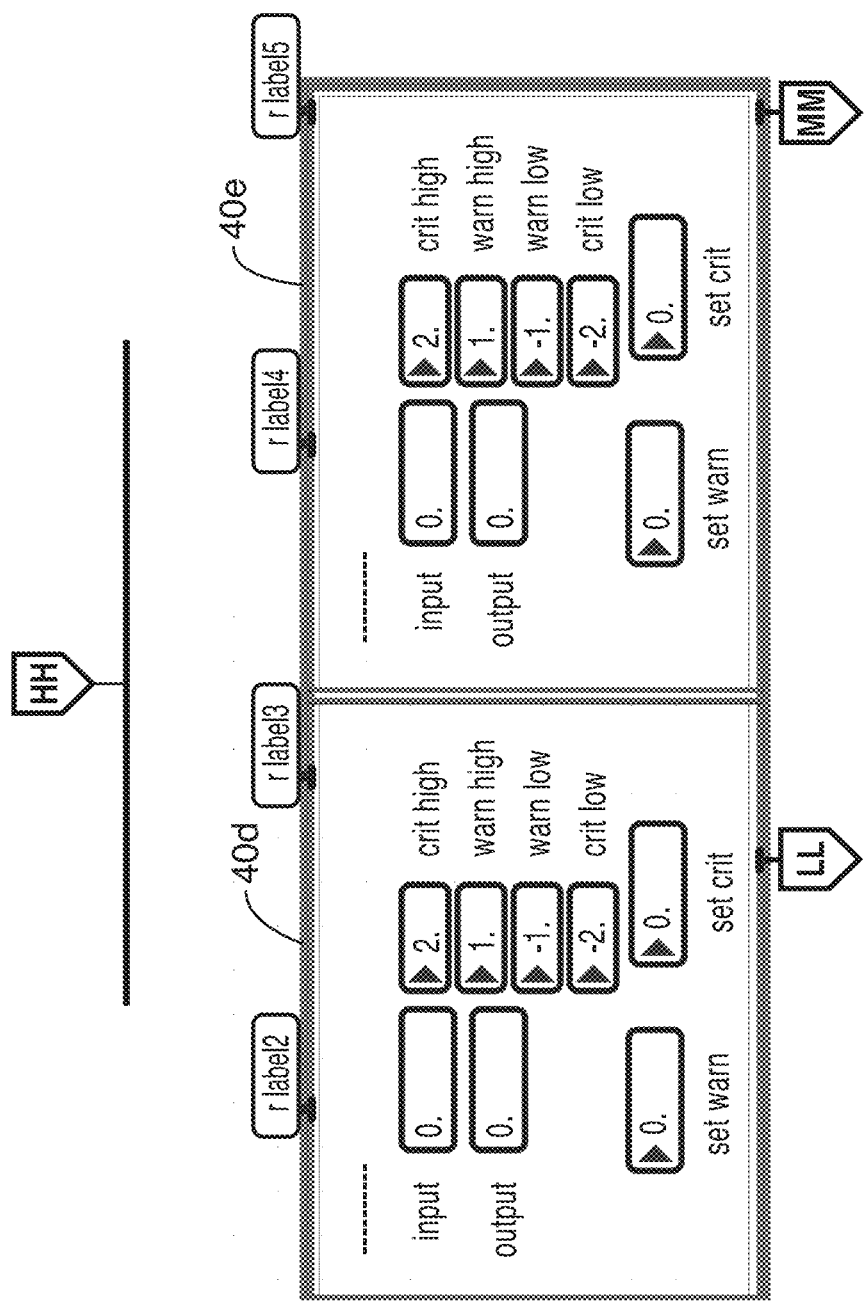
Figure 3D:
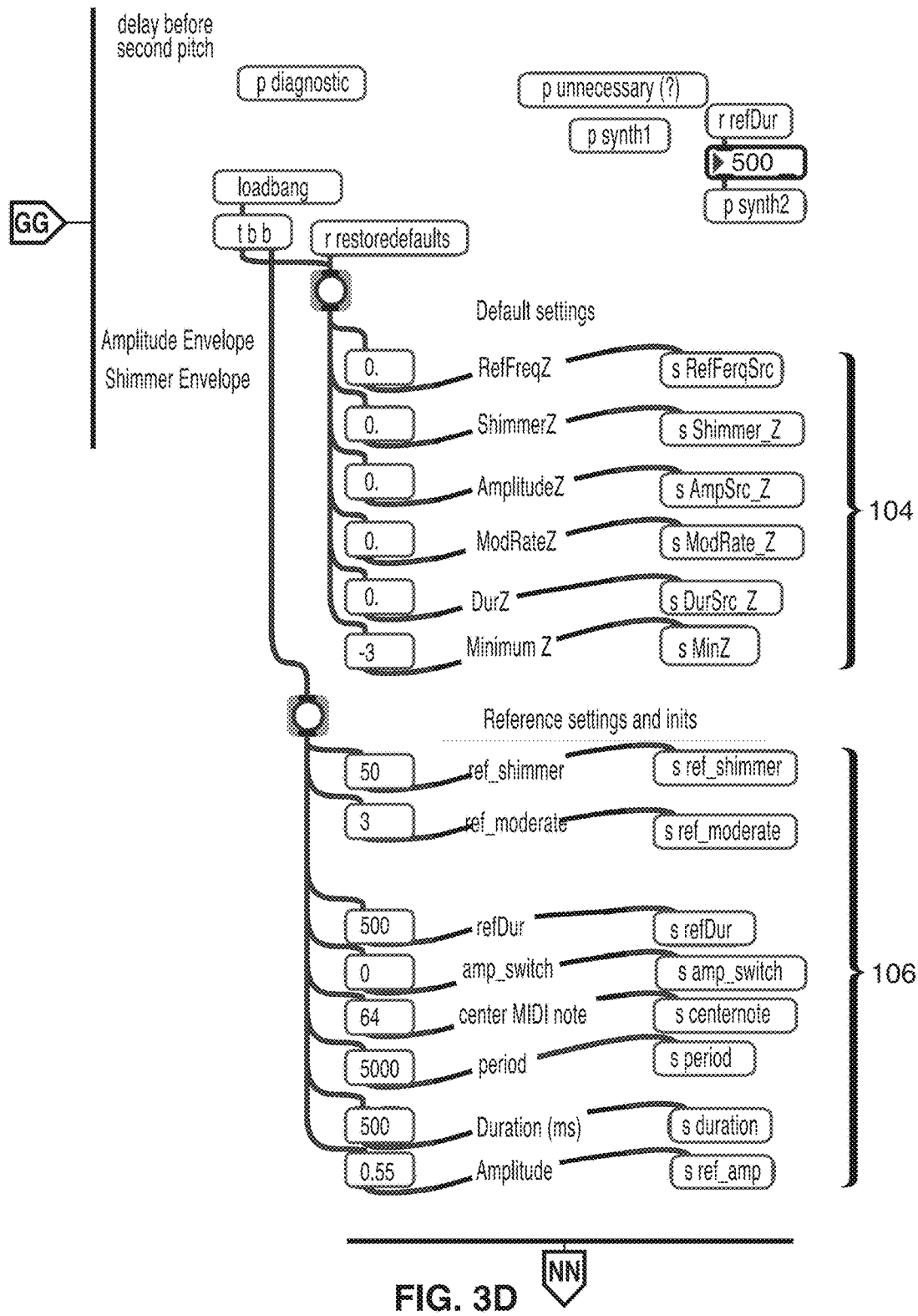
Figure 3E:
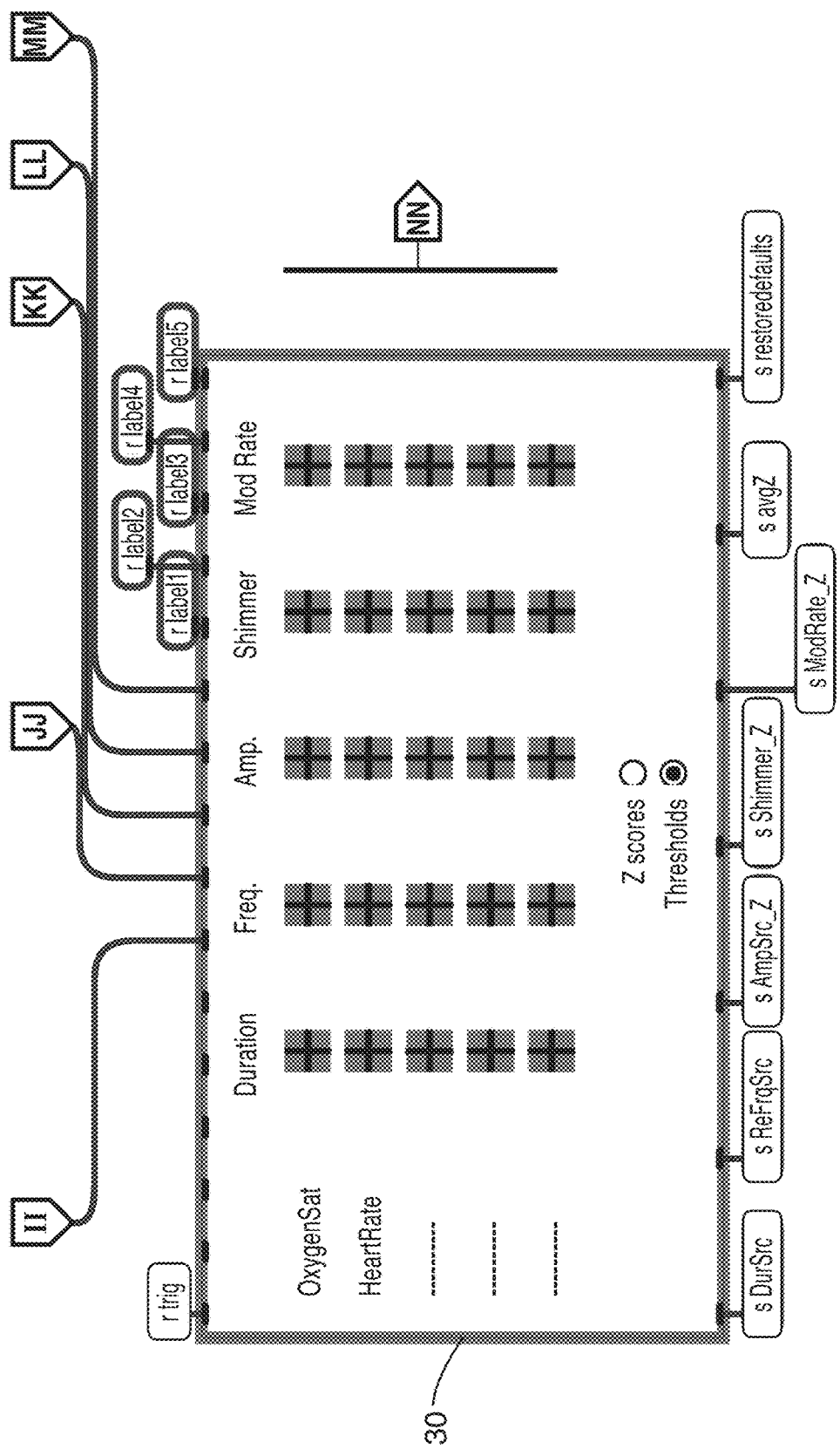
Figure 3F:
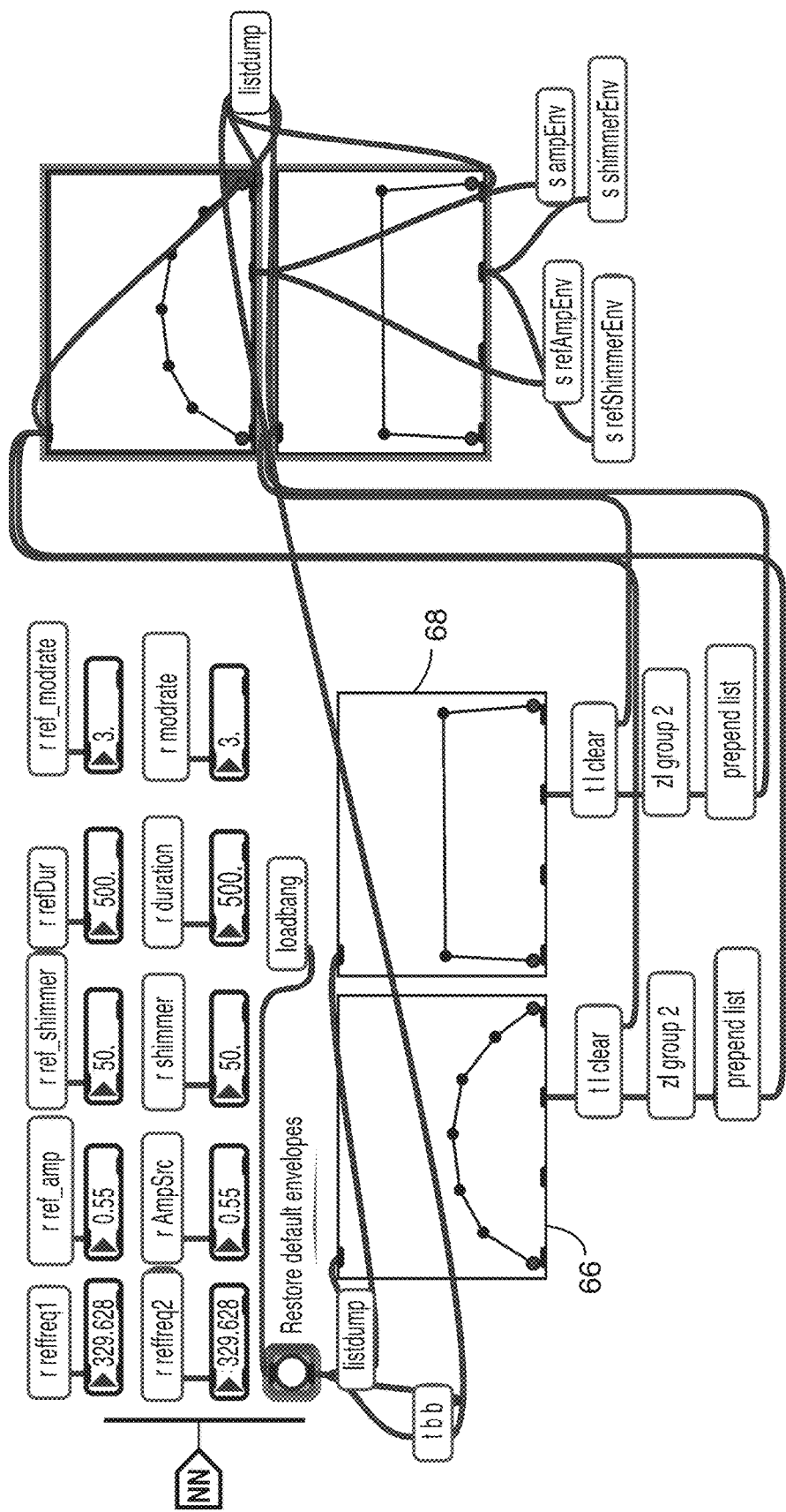
Figure 3G:
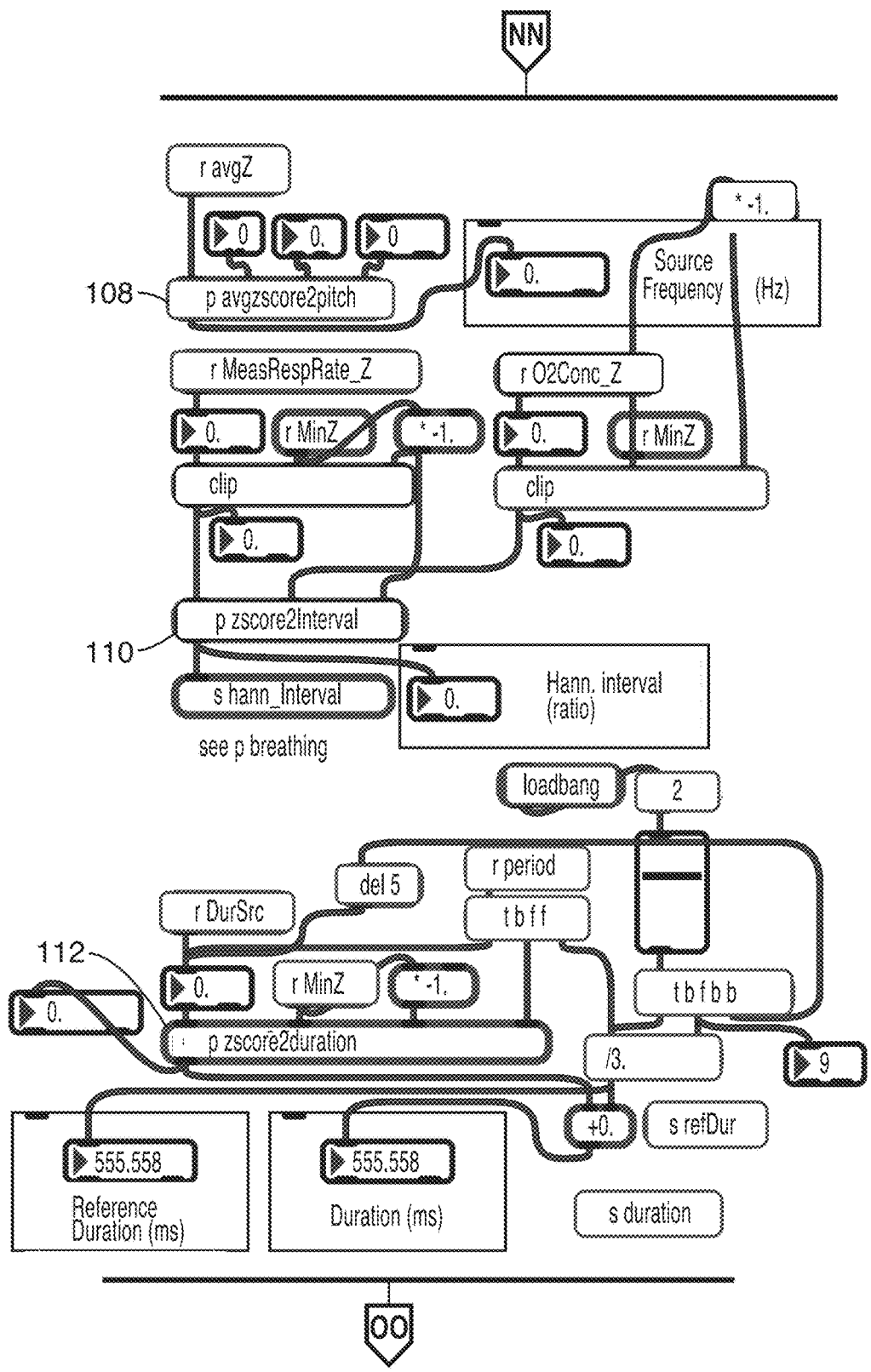

FIG. 3A through FIG. 3H illustrate a flow diagram for patch 100 designating interrelationships between the individual components underlying the front panel 60 shown in FIG. 2. This patch routes signals among the different sonification interface components (e.g. reader 20, and dynamic discretizer modules 40*a*-40*e* shown in detailed expanded views FIGS. 3A and 3C, and ultimately sends them to the "synth_simpleFM_improved" 102 and 122 (FIG. 3B), which renders the reference and actual state sounds, and sends those to the audio output (e.g. to speaker 72), or to an audio file as desired. Referring to the detailed view in FIG. 3D, the patch 100 also maintains default parameter settings 104 and reference settings 106 that are used to initialize the sonification, and the default amplitude 66 and modulation index 68 (shimmerEnv) waveforms (FIG. 3E).

Finally, the patch 100 routes z-score values to patches that convert z-scores to appropriate ranges of acoustic parameters, e.g. avgzscore2pitch 108, zscore2interval 110, zscore2duration 112, (shown in detailed view 3G), zscore2shimmer 114 (used in this sonification), zscore2modrate 116 (used in this sonification), zscore2amplitude 118, and zscore_melodic_interval 120 (shown in detailed view 3H).

Figure 4:
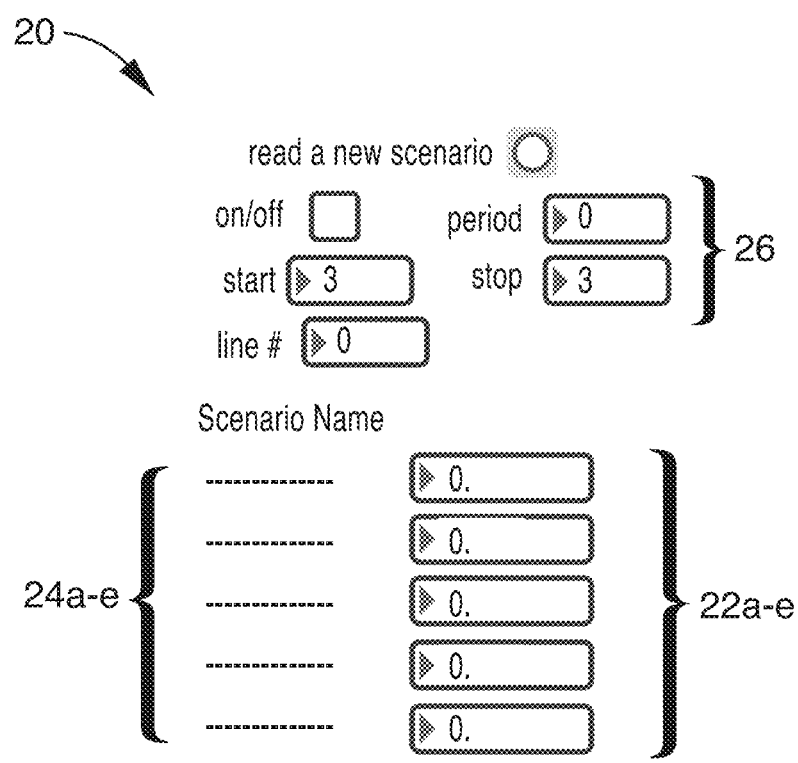
FIG. 4 is a detail view showing an example of the user-interface view of the new data reader patch of FIG. 2.
Figure 5A:
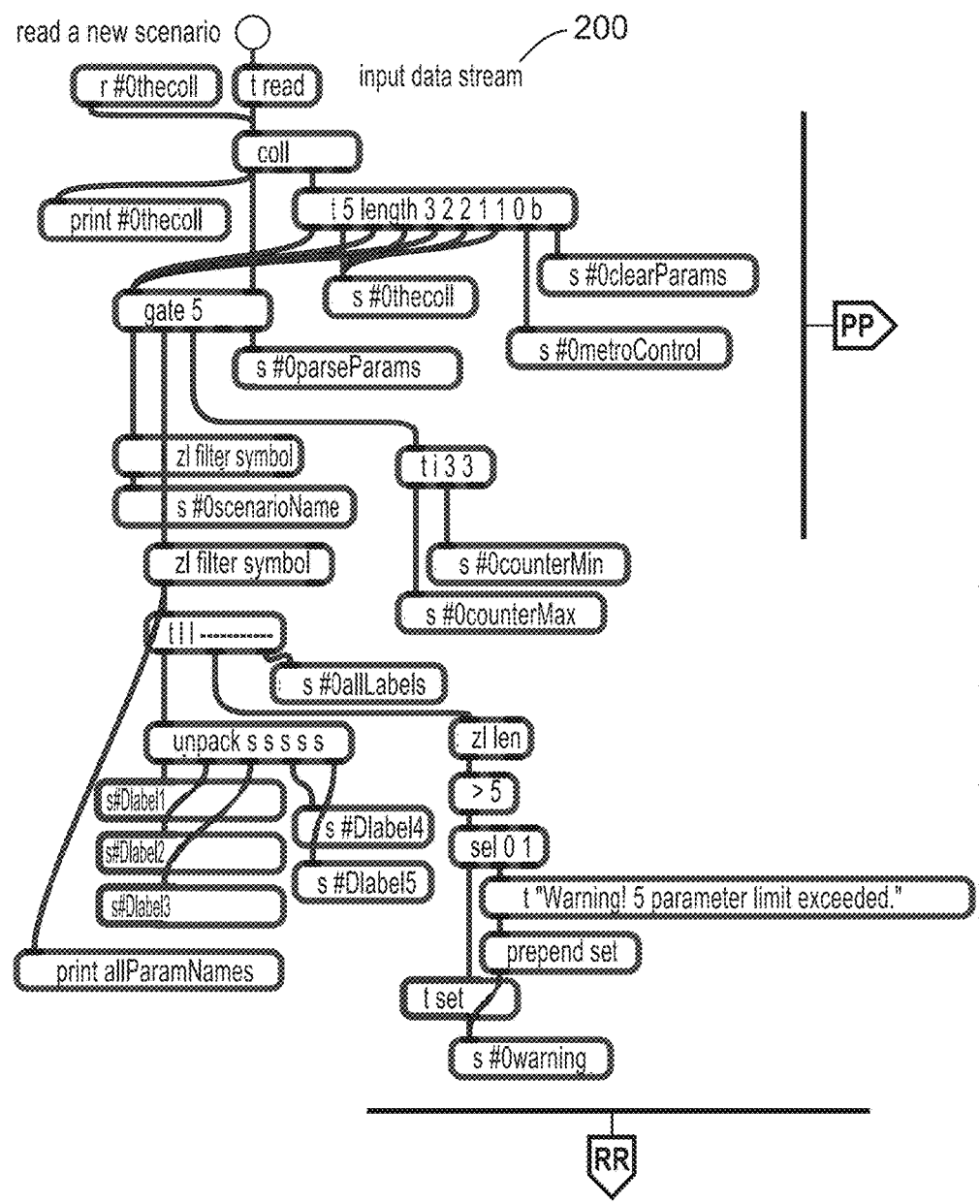
FIG. 5A through FIG. 5D show a flow diagram of the new data reader patch of FIG. 4.
Figure 5B:
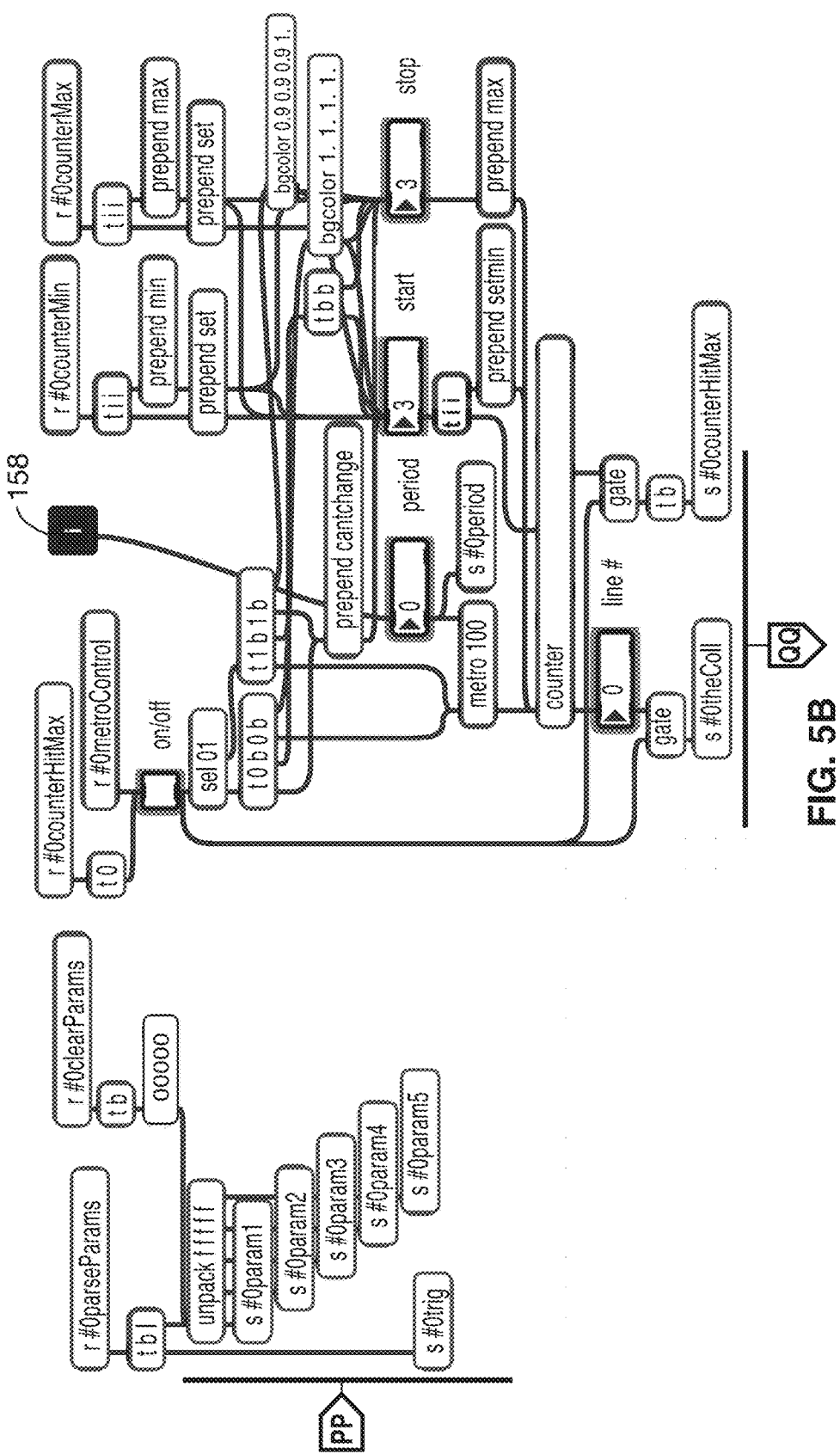
Figure 5C:
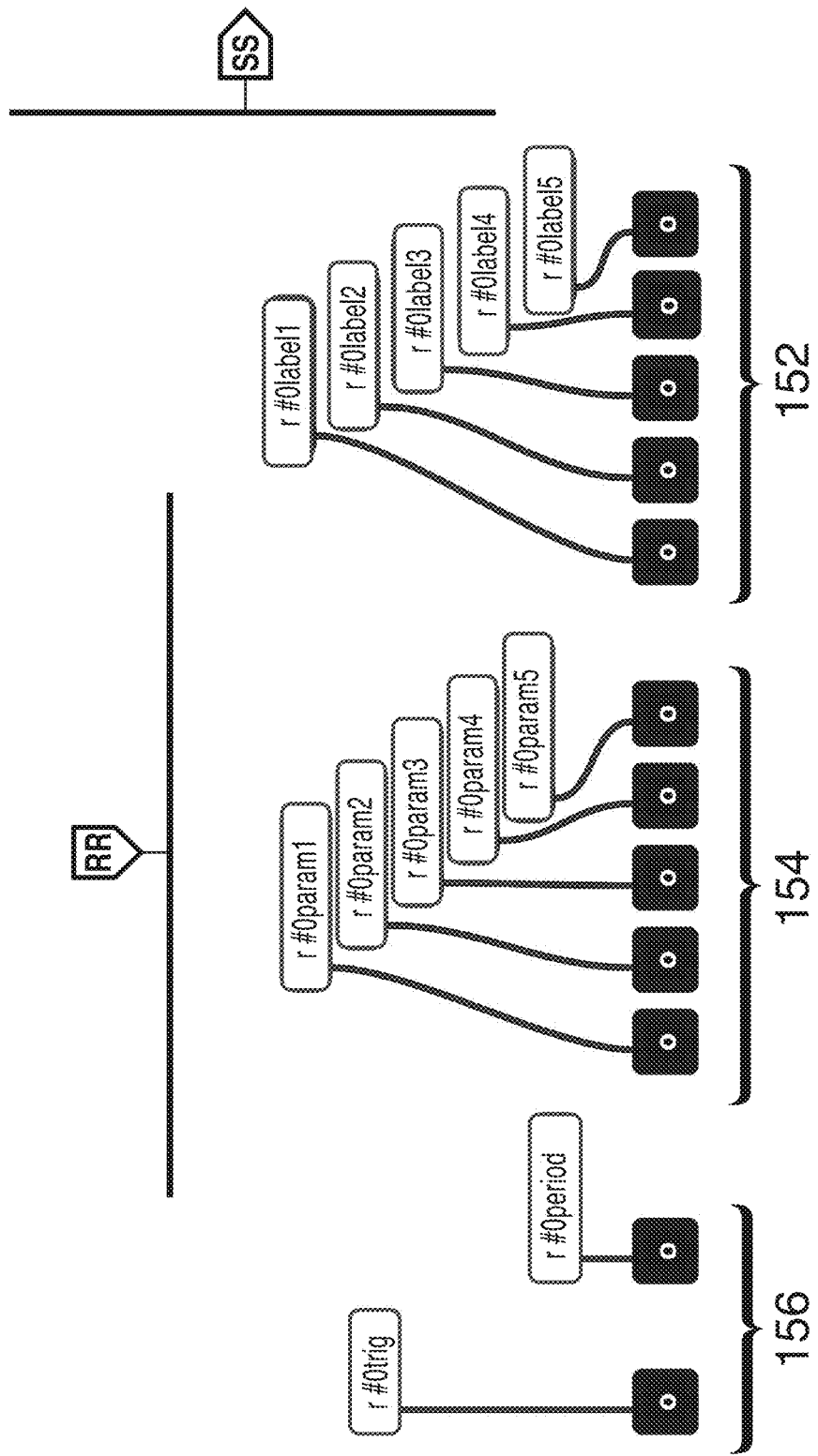
Figure 5D:
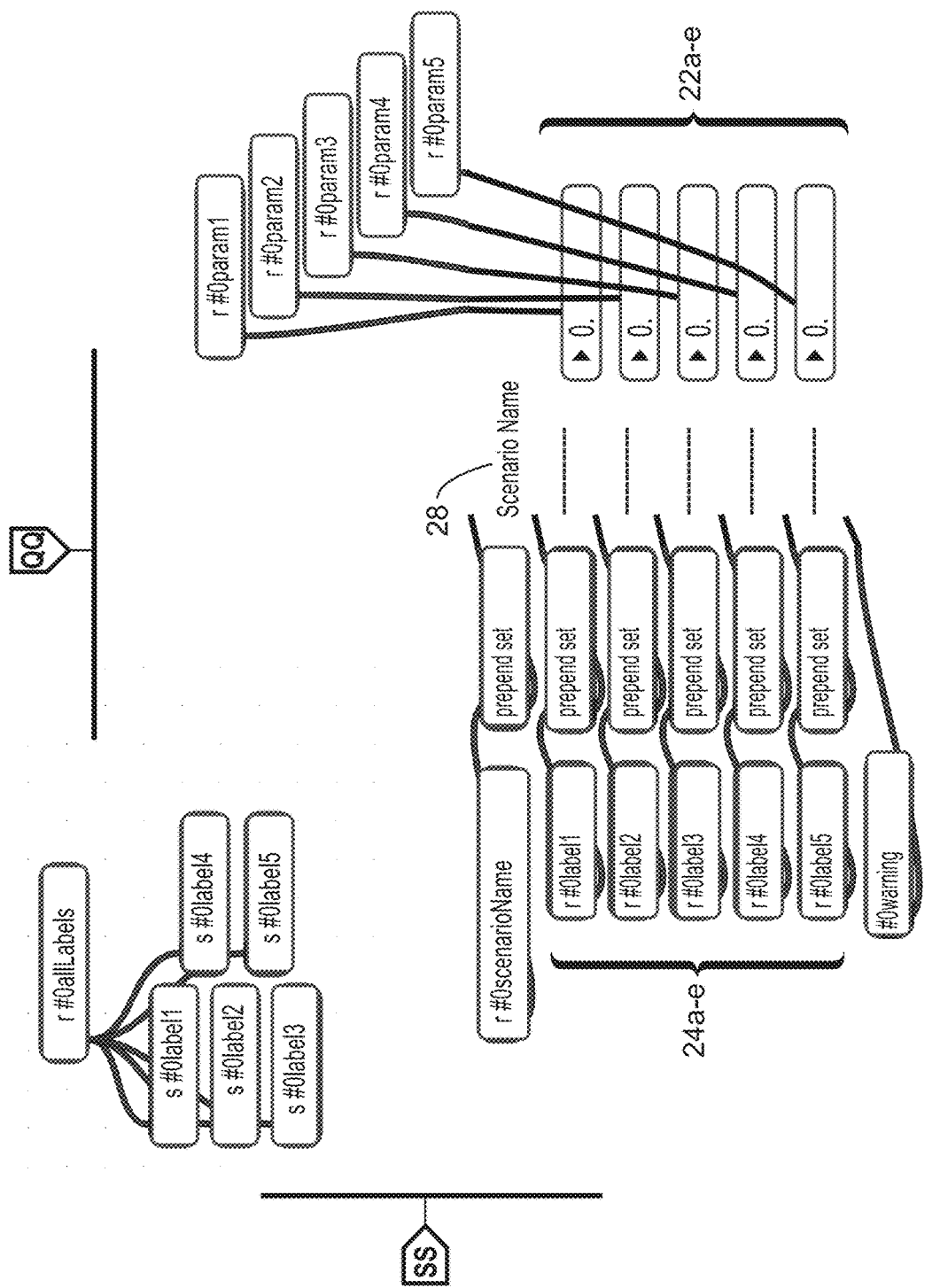

FIG. 4 is a detail view showing an example of the user-interface view of the "new_data_reader" patch 20.

FIG. 5A through FIG. 5D show a flow diagram 150 of the "new_data_reader" patch 20 of FIG. 4. One of ordinary skill in the art will appreciate the design of this module to dynamically set the names of signals used throughout the sonification based on the values in the input data stream 200 (here read into the Max coil object, FIG. 5A). Referring to detailed views 5B and 5C input 158 and outputs 152, 154 and 156 are shown with corresponding grey boxes.

Figures 6, 7:
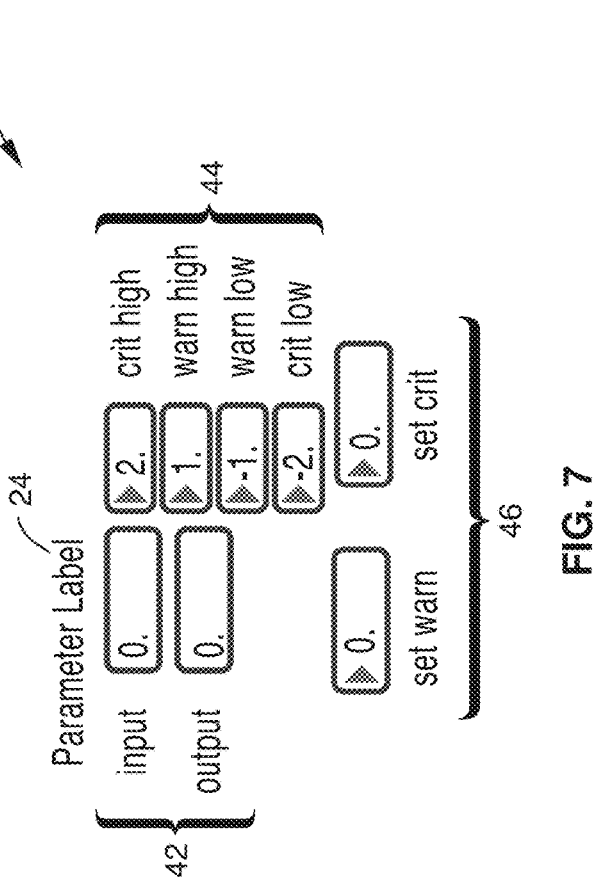
FIG. 6 shows the contents of the sample data stream used to generate the sounds used in the experiments described herein.
FIG. 7 is a detail view showing an example of the user-interface view of the dynamic discretize patch of FIG. 2 for a particular parameter.

FIG. 6 shows the contents of the sample data stream 200 used to generate the sounds used in the experiments described herein. The first row 202 of data stream 200 contains the scenario name, the second row 204 contains the column labels for the respective physiological parameters, and subsequent rows 206 contain the parameter values. The value before the comma in each row is the time step. This embodiment is only one of many possible embodiments, and the data parser can be written to parse any organized data stream in which timestamps and named parameter values are present.

FIG. 7 is a detail view showing an example of the user-interface view of the "dynamic_discretize" patch 40 for a particular parameter 24.

Figure 8:
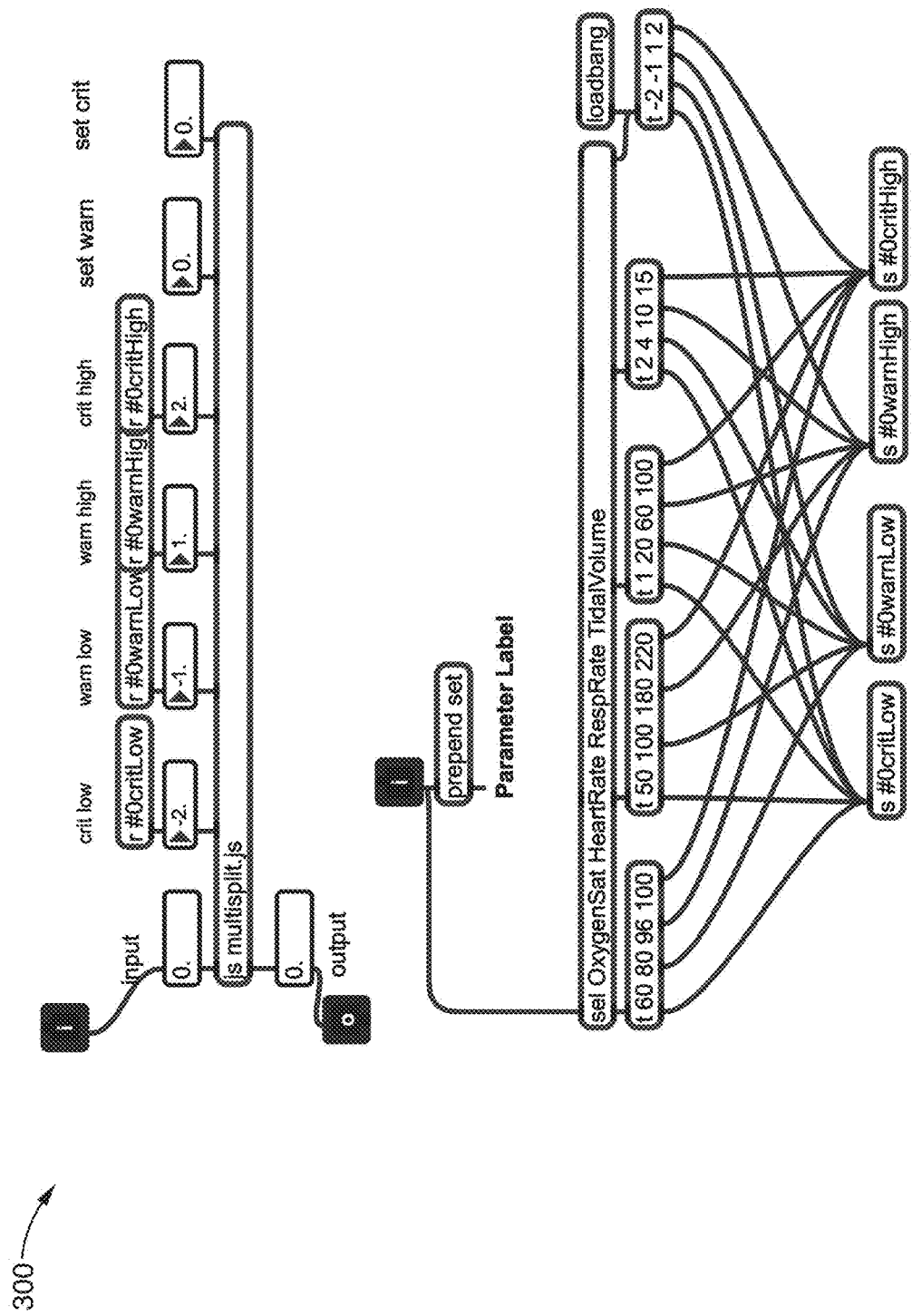
FIG. 8 is an example of the flow diagram of the dynamic discretize patch of FIG. 2.
Figure 8A:
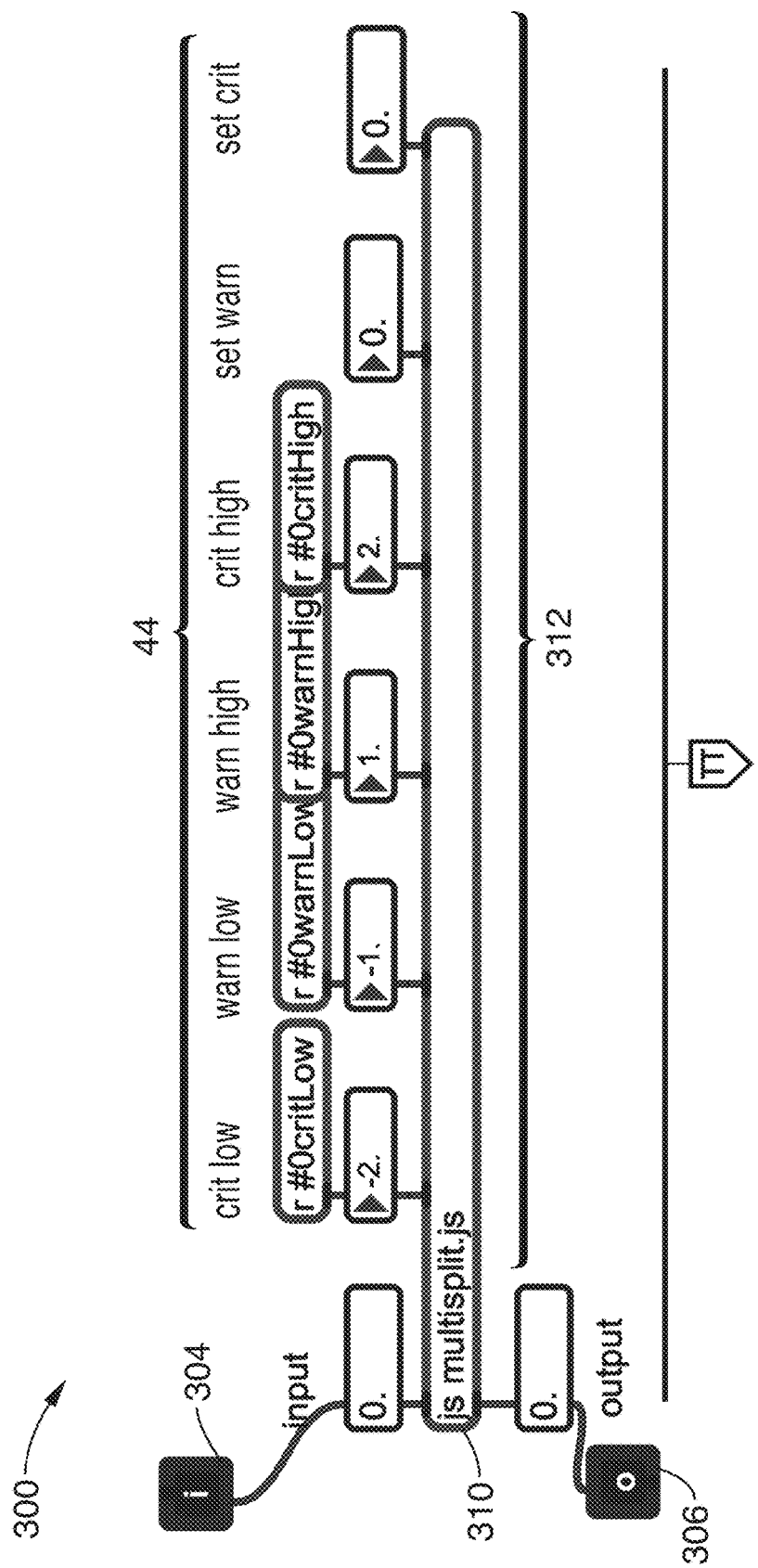
FIG. 8A through FIG. 8B show detailed expanded views of the flow diagram of FIG. 8.
Figure 8B:
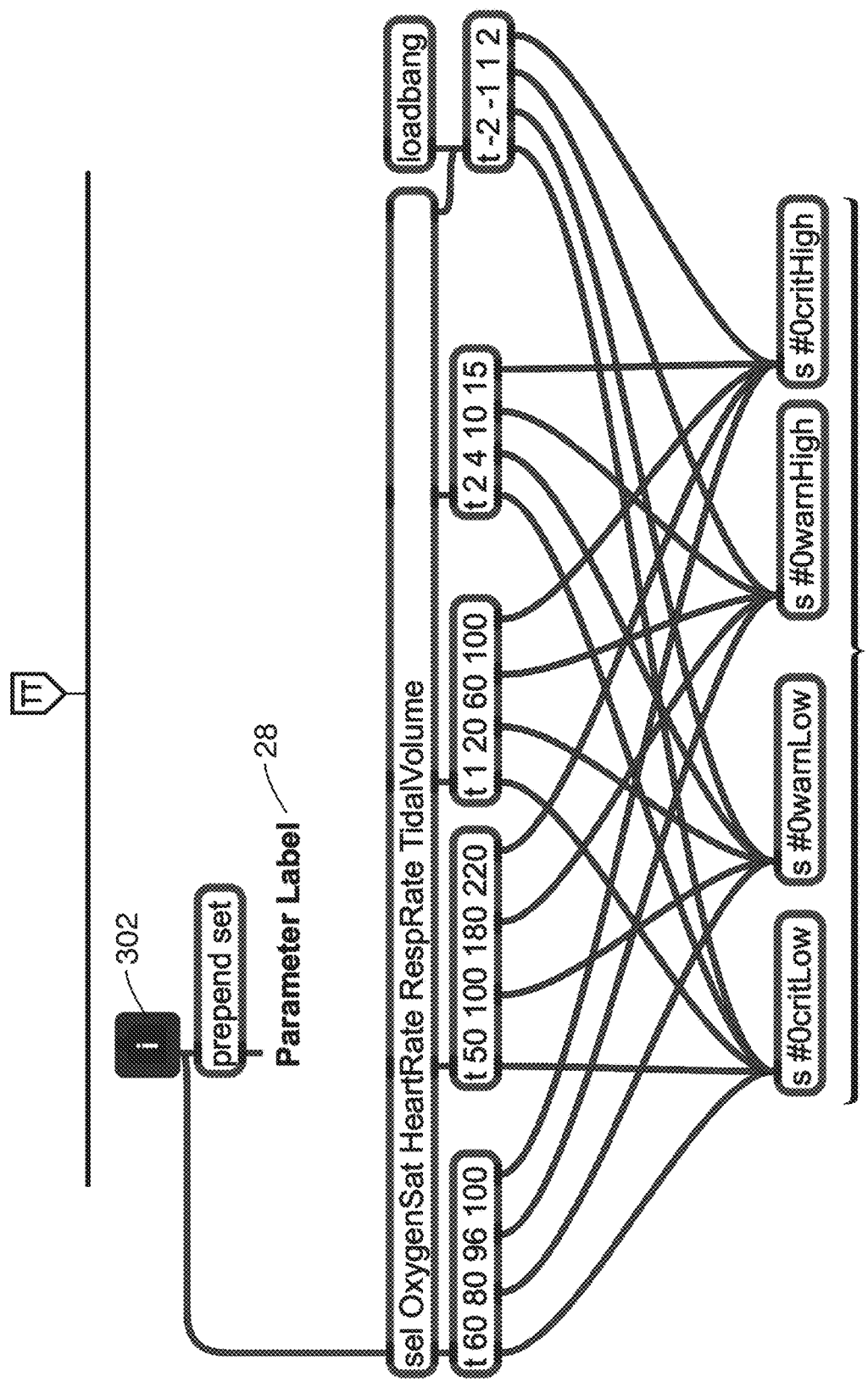

FIG. 8 is an example of the flow diagram 300 of the "dynamic_discretize" patch (40*a* through 40*e*). Based on the parameter label present at the lower 302 of the two input ports (302, 304 and 306 shown in detailed views FIGS. 8A and 8B) the four category thresholds are set appropriately (via the t objects) for the units in which the physiological parameters are measured. Here, the thresholds are set for a specific embodiment. The desired thresholds can vary between clinical scenarios or across time within a clinical scenario. One of ordinary skill in the art will recognize that the setting of the threshold values can easily be converted from the static representation shown here to a dynamic setting based on the scenario. The JavaScript object multi-split.js 310 accomplishes the conversion from the category labels, e.g. "warn Low," to the appropriate output category value 312 (e.g. −2, −1, 0, 1, 2).

Figure 9:
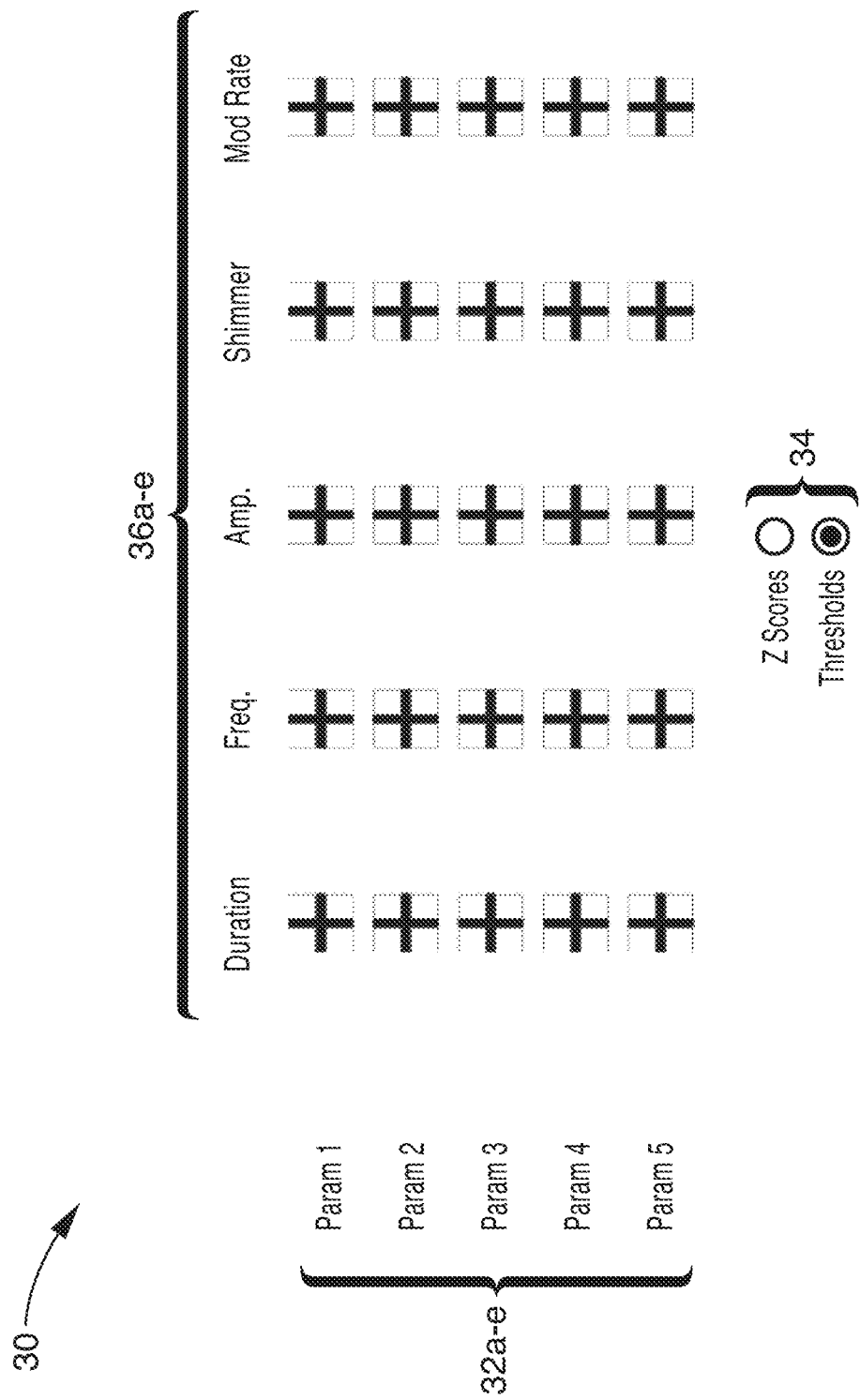
FIG. 9 is a detail view showing an example of the user-interface view of the dynamic router patch shown in FIG. 2.

FIG. 9 is a detail view showing an example of the user-interface view of the dynamic router patch 30 shown in FIG. 2.

Figure 10A:
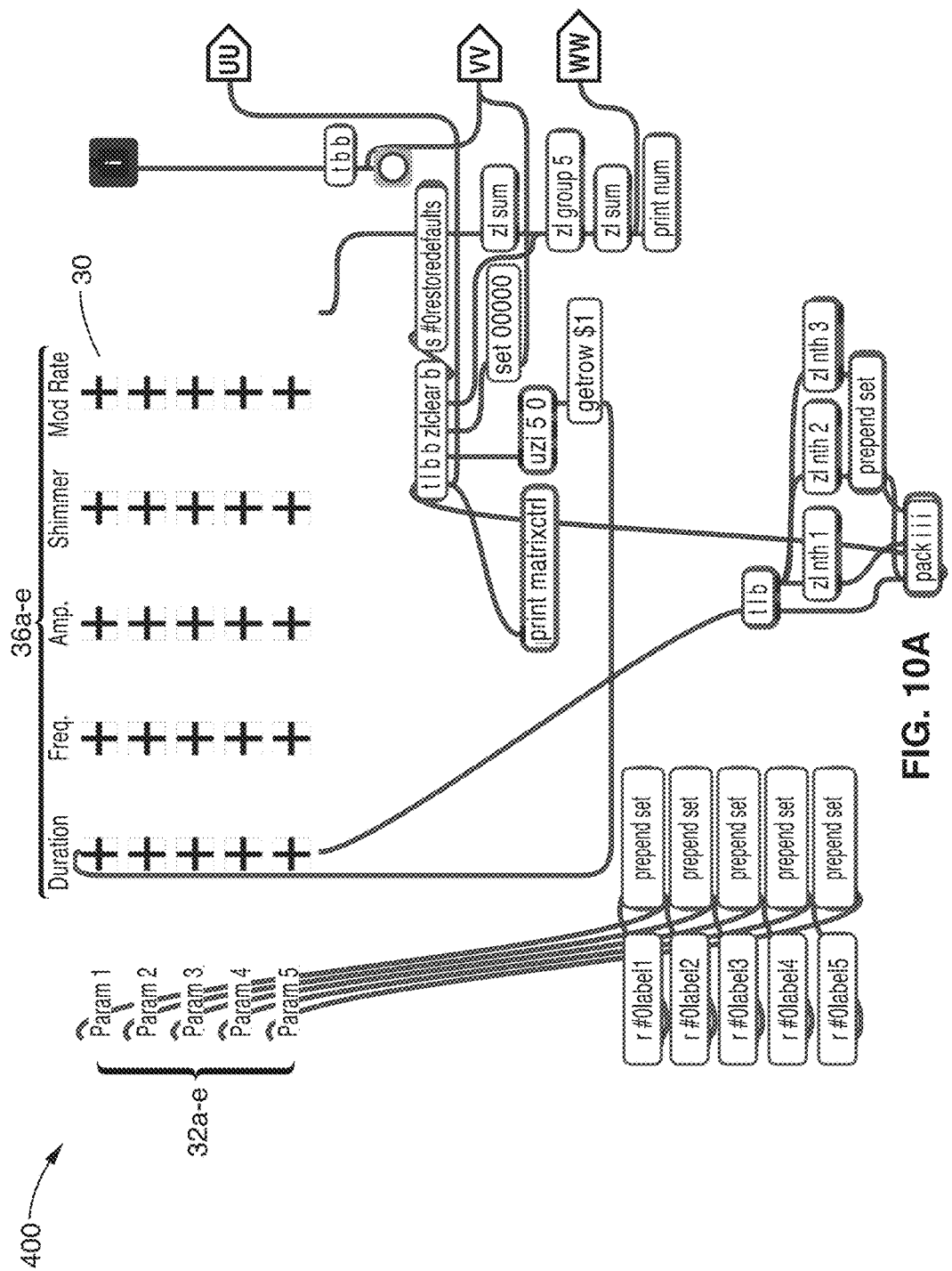
FIG. 10A through FIG. 10B show a flow diagram of the dynamic router patch of FIG. 2.
Figure 10B:
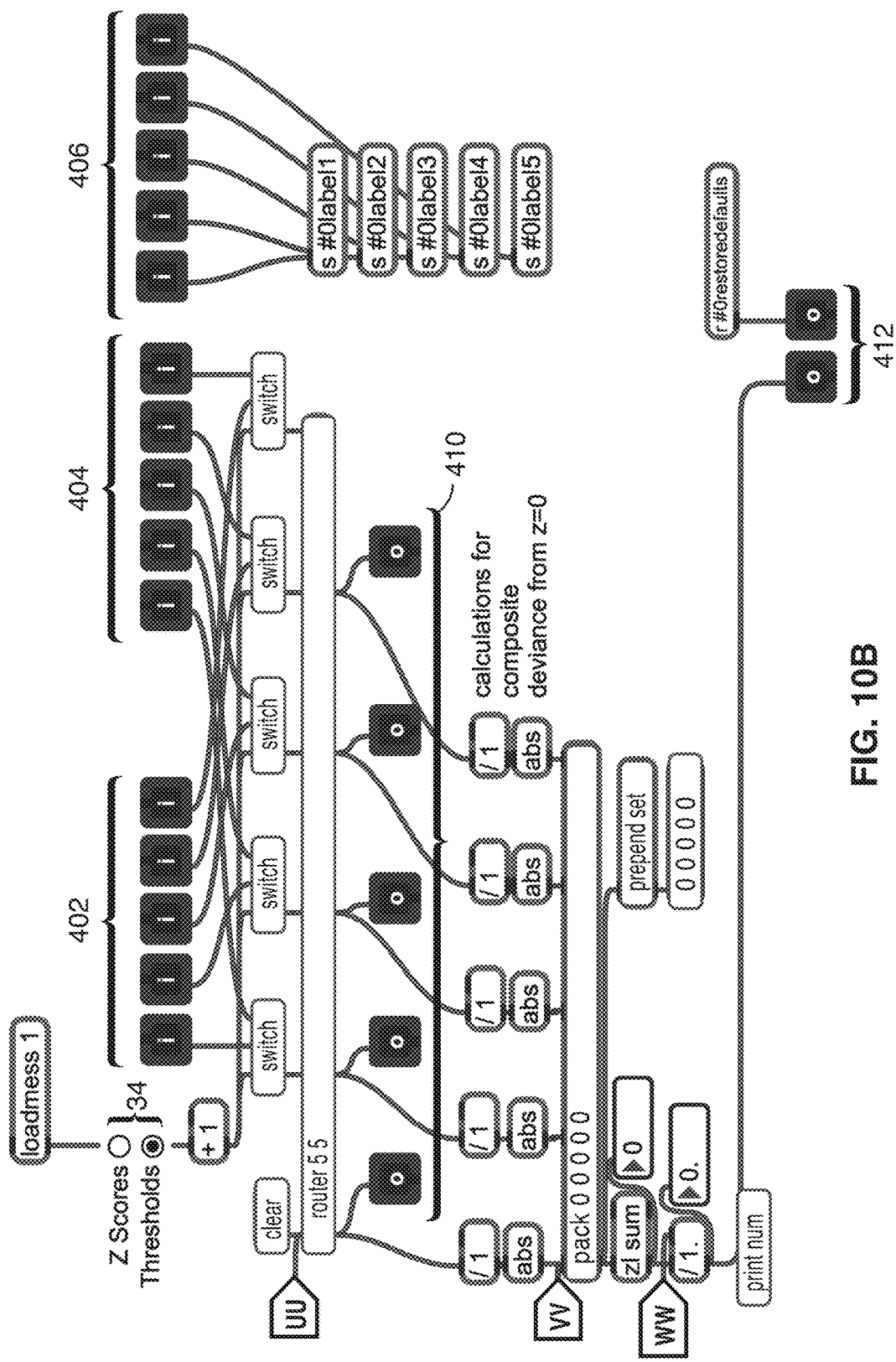

FIG. 10A through FIG. 10B show a flow diagram 400 of the dynamic router patch 30 of FIG. 2. FIG. 10A through FIG. 10B show detailed expanded views of the flow diagram of FIG. 10. One of ordinary skill in the art will recognize that this patch manages the mapping of dynamically set input parameters corresponding to the physiological variables 32*a*-32*e* to five acoustic variables 36*a*-36*e*, and routes those input values 402, 404, 406 to the selected outputs 410, 412. In addition, the patch 30 is configured to calculate a composite average deviation across physiological input parameters 32*a*-32*e*.

Figure 11:
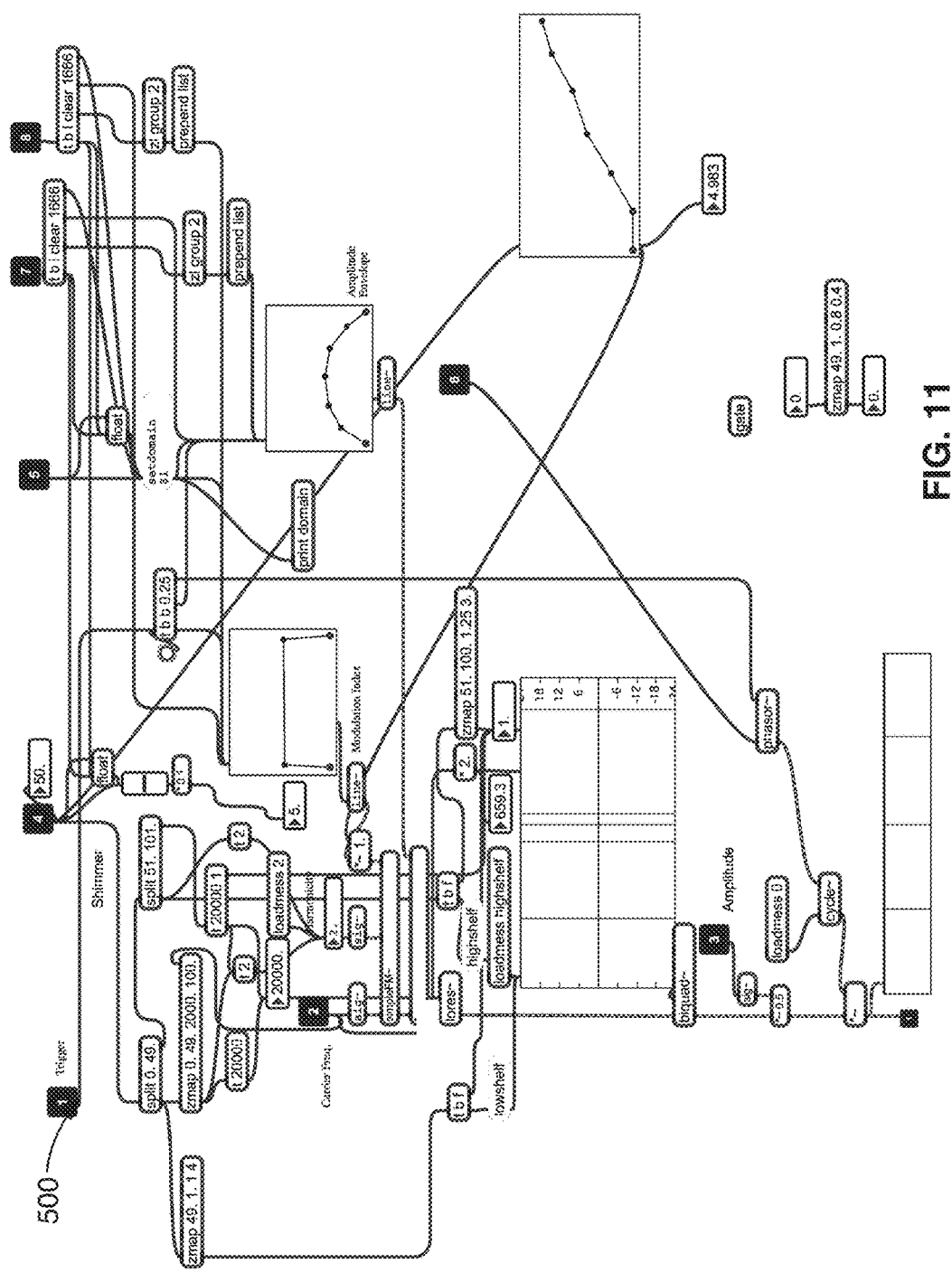
FIG. 11 is a flow diagram of the sound synthesis patch shown in FIG. 2.
Figure 11A:
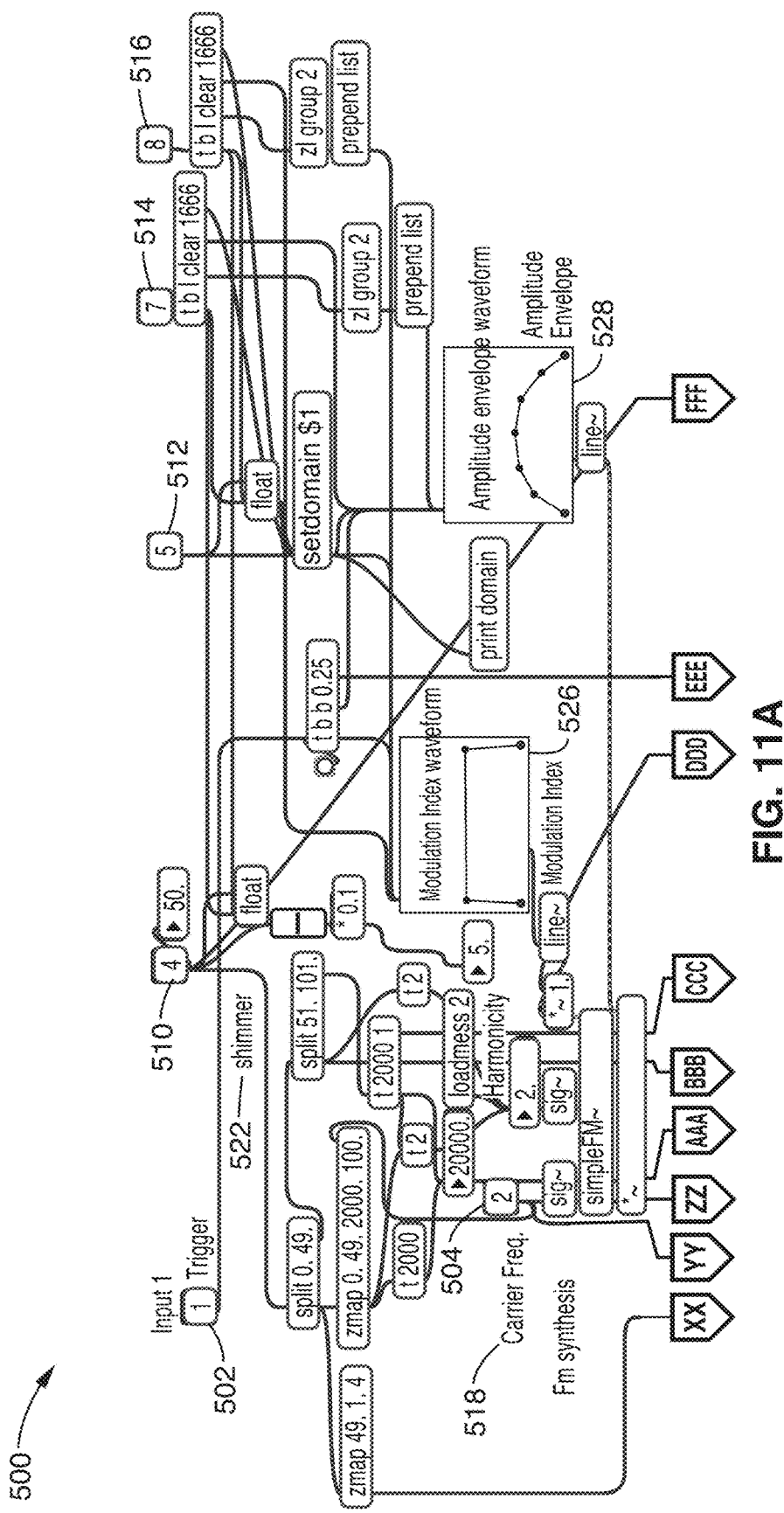
FIG. 11A through FIG. 11B show detailed expanded views of the flow diagram of FIG. 11.
Figure 11B:
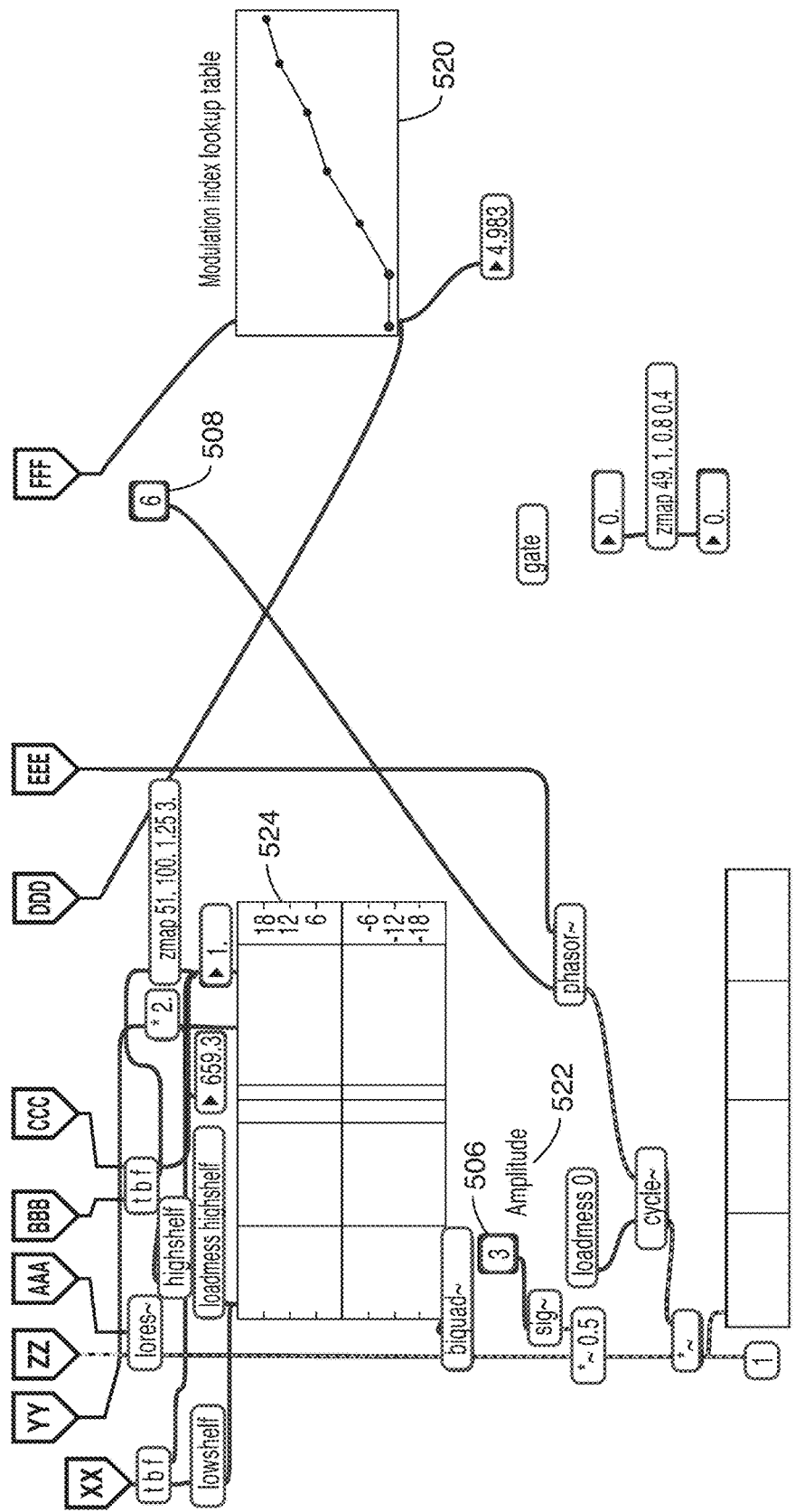

FIG. 11 is a flow diagram 500 of the of the sound synthesis patch synth_simpleFM_improved 122 shown in FIG. 2. FIG. 11A through FIG. 11B show detailed expanded views of the flow diagram of FIG. 11. The patch 500 accepts eight input parameters (brown boxes with numbers 1 through 8 surrounded by gray borders) to configure the sound synthesis. Input 1 (502) triggers the generation of a sound. Input 2 (504) sets the carrier frequency 518 of the frequency modulated tone. In this particular embodiment, the carrier frequency is always set to 329.628 Hz. Input 3 (506) sets the overall amplitude 522 of the tone. Input 4 (510) receives the degree of shimmer on a scale between 0 and 100.

Figure 3H:
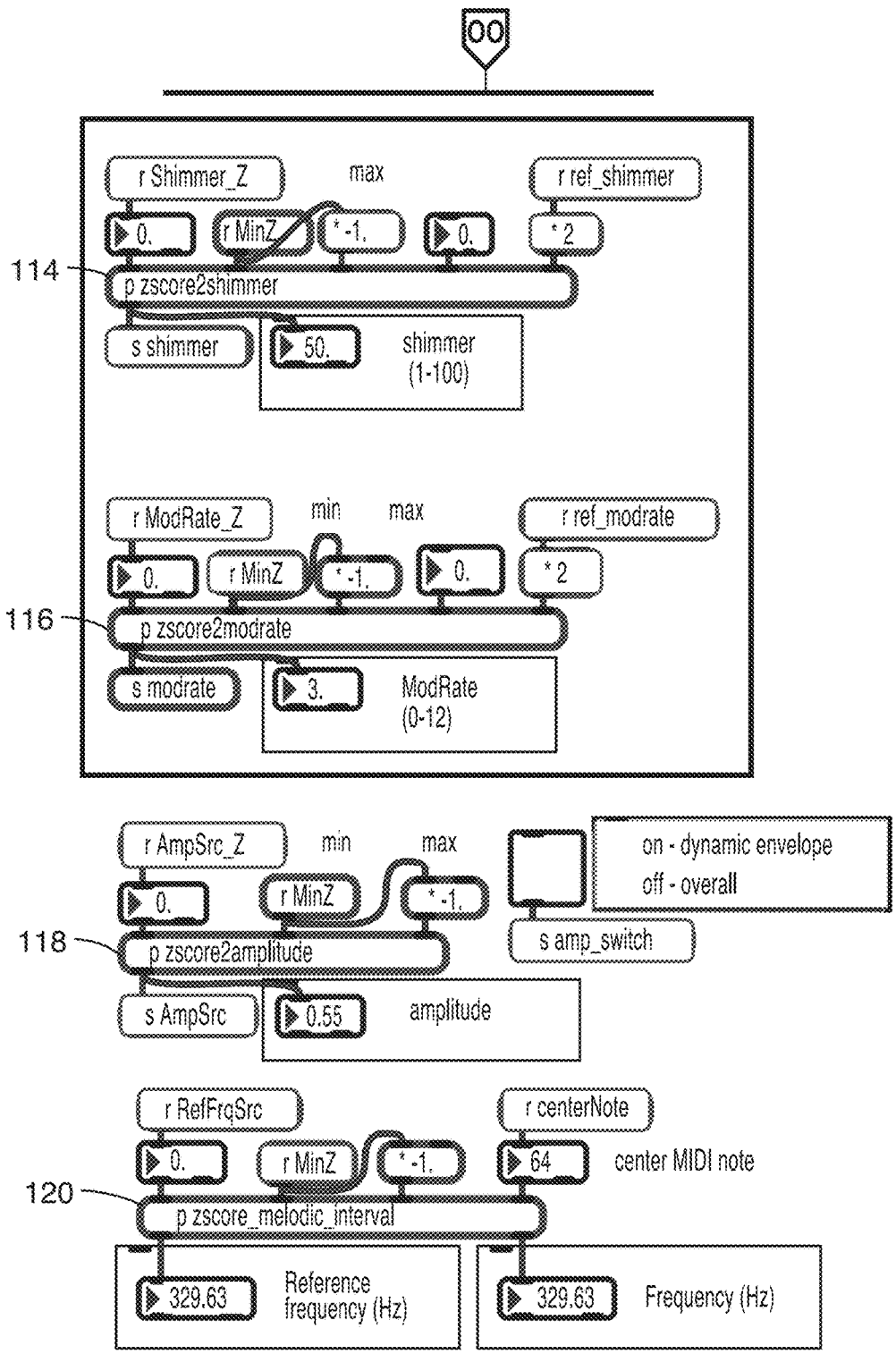

The z-score category (z=−2, −1, 0, 1, 2) is transformed to the 0-100 scale by the zscore2shimmer patch 118 shown in FIG. 3H. The shimmer values are further processed to 1) set the filter properties of a biquad~ filter object 524 that accentuates low frequencies in the case of z<0 and high frequencies in the case of z>0. The shimmer value 522 is also used to read out a modulation index value from a mapping function (modulation index lookup table 520) which, when multiplied together a modulation index waveform 526, sets the time-varying modulation parameter sent to simpleFM~. The modulation index waveform 526 is set by the Input 8 (516), and can either assume a trapezoidal shape as shown here, or can be generated by the dynwvf patch to generate a time-varying waveform with a transient increase in the amplitude modulation index to connote added "urgency."

Similarly, Input 7 (514) determines the overall shape of the amplitude 528 envelope applied to the sound. Input 6 (508) specifies the number of amplitude modulations applied to the sound, and in this embodiment is based on the HeartRate parameter. Input 5 (512) sets the overall duration of the sound. Note, the patch is designed such that the respective amplitude modulation 528 and modulation index 526 waveforms are applied dynamically across the entire duration of the sound.

Figure 12:
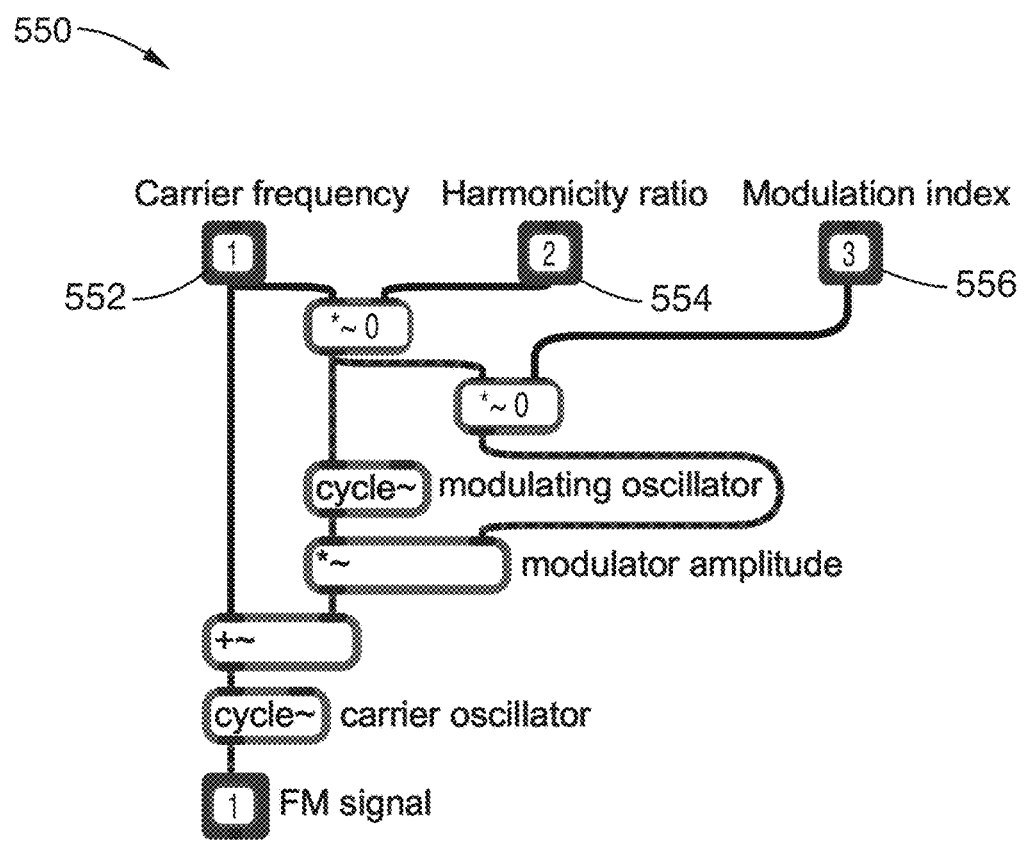
FIG. 12 is a flow diagram for the FM synthesis patch shown in FIG. 2.

FIG. 12 is a flow diagram for the FM synthesis patch (simpleFM~) 550. Inputs 552, 554 and 556 are provided for carrier frequency, harmonicity ration and modulation index respectively.

Note also that the dynamic waveform controls the modulation index of the FM synthesis and thereby varies the amount of shimmer and dissonance within each discrete sound. Optionally, the dynamic waveform can be shaped to, for example, give added "urgency" to the sound. Also, while any given dynamic waveform shape will generate a specific sound, varying the dynamic waveform shape increases the range of sounds that can be employed with the technology described herein beyond those provided as examples herein.

Figure 13:
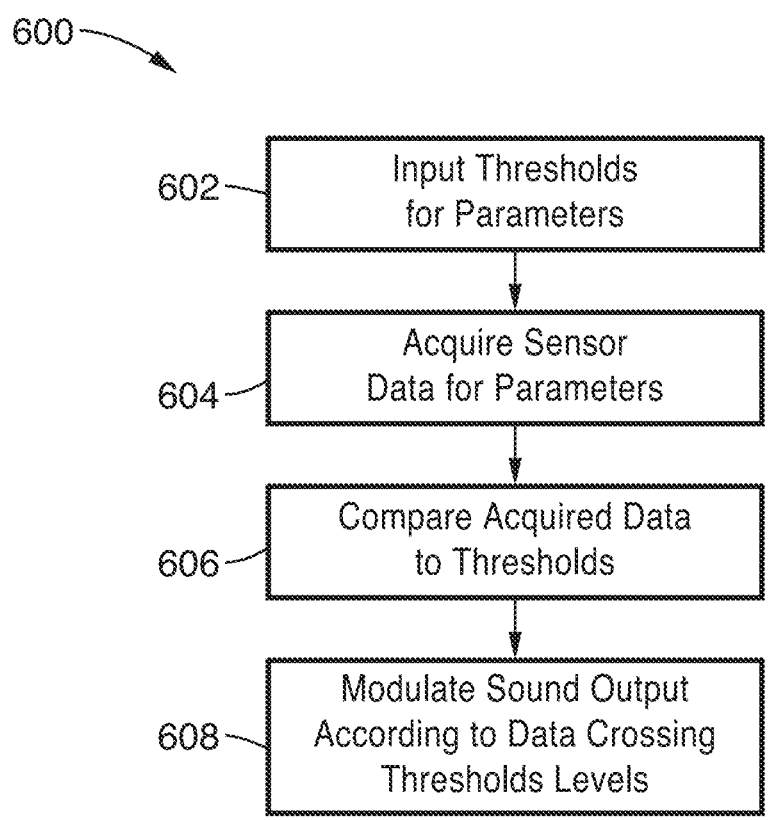
FIG. 13 shows a flow diagram of the method for generating a sonification output for data relating to one or more physiological parameter.
Figure 14A:
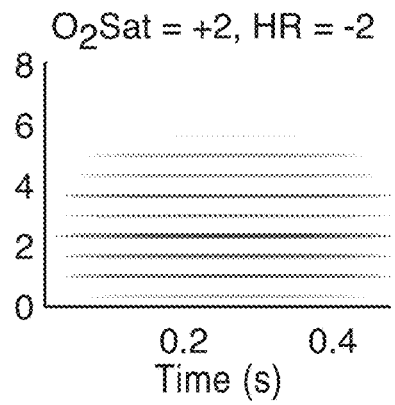
Figure 14B:
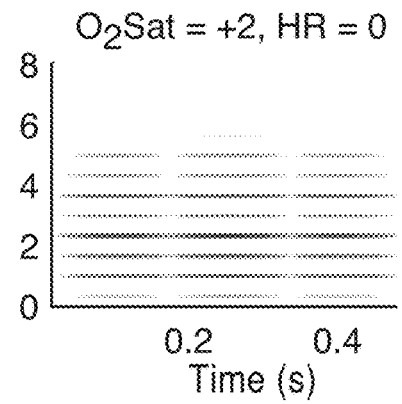
Figure 14C:
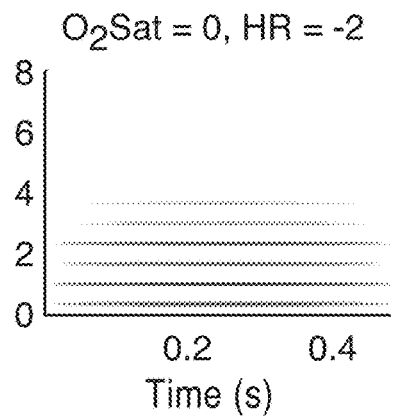
Figure 14D:
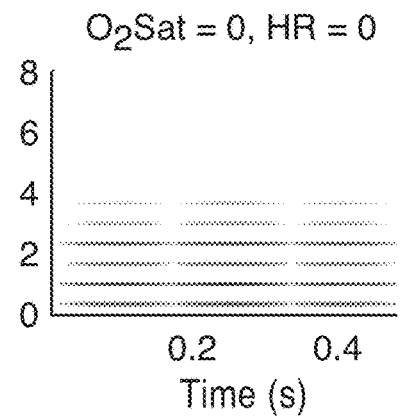
Figure 14E:
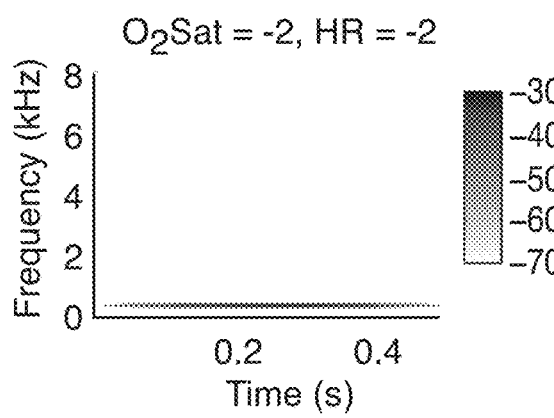
Figure 14F:
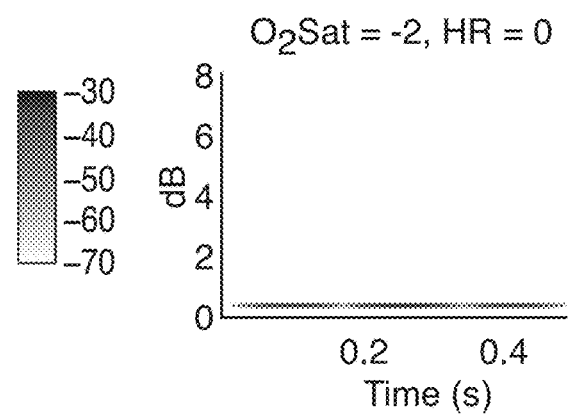

FIG. 13 shows a flow diagram of method 600 for generating a sonification output for data relating to one or more physiological parameter. Method 600 is embodied in both the detailed software implementation described above for FIG. 2 through FIG. 12, as well for obtaining the experimental results below.

At step 602, the user inputs thresholds (e.g. threshold values 22a through 22e in FIG. 2A) for each of the physiological parameters (e.g. 24a through 24e in FIG. 2A) being measured.

At step 604 sensor data for each of the parameters is acquired (e.g. data 200 shown in FIG. 6).

At step 606, the acquired data is compared to the set thresholds 22a through 22e.

At step 608, the sonification output is modified (e.g. according to the patch 500 shown in FIGS. 11A and 11B) according to the particular z-score that the data 200 falls into.

Experimental Results

Across two experiments, clinical practitioners were tested on their ability to 1) discriminate pairs of sounds ("two-note discrimination" task), 2) infer and discern the intended physiological connotation of each acoustic attribute ("name the variable" task), and 3) categorize the amount of change in an implied physiological variable into 3 levels of change: None, Small, and Large ("change magnitude" task).

Considerable variation in performance was observed across the set of practitioners, ranging from near perfect performance on all tasks, even with no prior exposure to the stimuli, for failure to reach a target accuracy criterion of 87.5% after ~80 minutes of training. On average, performance was well above chance on the "name the variable" and "change magnitude" tasks during initial exposure and reached criterion within ~20 minutes of training on each task.

Experiment 1

The specific objective of this experiment was to assess the ability of naïve participants to discriminate between relatively subtle acoustic manipulations of sounds intended to convey information about heart rate and oxygen saturation levels, and to associate those sounds with those physiological variables. The experiment was designed to step participants through three tasks of increasing difficulty, with feedback, to emulate a situation with limited training. Note that the purpose of the experiments was not to measure the perceived aesthetic qualities of the sounds or how apparent the intended semantic mappings were. Thus, the descriptions of the acoustic design principles reflect experimenter intuitions rather than experimentally established associations.

Sixteen staff members (14 female) aged 24-69 years (mean±std: 43.8±14.7) from the Intensive Care Nursery (ICN) at the Children's Hospital at Dartmouth (CHaD) participated in the experiment.

Stimuli for the experiment were designed and rendered using Max/MSP software (Cycling '74, San Francisco Calif.). An overarching strategy was adopted in which the physiological signals were represented in terms of standardized z-scores. Acoustic parameters would then be set such that a single value of the parameter represents a range between two standard deviation levels, e.g., the mean and a decrease or increase of one standard deviation. The net effect of this strategy is that continuous variation in physiologic and acoustic values is constrained to a limited number of categories.

Heart rate was represented by the rate of amplitude modulation (AM) of the sound. The SDU level of z=0 was represented by three cycles within the 500 ms period (6 Hz). Each increasing or decreasing step in z was associated with the addition or subtraction of 1 cycle, respectively.

Initial discussions with Intensive Care Nursery staff indicated this was a promising approach to pursue, given that listeners could learn to associate acoustical characteristics with fixed levels of deviation, but the specific target levels (means) and deviation ranges of any given physiological parameter could be set on a case-by-case basis as appropriate.

The fundamental/carrier frequency of the sounds was set at 329.6 Hz (E4). The duration of each sound was 500 ms and the silent interval between them was 750 ms.

Spectrograms of six of the 25 sounds that were used for the sonification are illustrated in FIG. 14A through FIG. 14F. Highlighted across rows is the timbral variation that was used to denote different levels of oxygen saturation. The two columns denote different levels of heart rate with the column on the right with three pulses indicating a level of z=0.

Participants were seated in front of a computer in a comfortable small, quiet, and dimly lit room. Audio stimuli were presented via desktop speakers at a comfortable volume. Data collection was implemented in Ensemble, a web-based application for stimulus presentation and data collection. Stimulus selection was performed with MATLAB (Mathworks, Natick Mass.) scripts expressly written for the experiment. The experiment was divided into several tasks as described below. The order of the tasks was arranged so as to minimize the degree of performance anxiety experienced by individuals unaccustomed to the idea of having to consciously discern subtle changes in sounds. Because a primary objective was to evaluate performance in the context of a training scenario, participants were provided with feedback following every trial in every condition. Following completion of the tasks, participants answered a series of questions about their perceived listening abilities and the perceived difficulty of the tasks.

Participants were first presented with a task that requires a judgment about whether two sounds are the same or different ("two-note discrimination task"). While the sounds ultimately represent specific physiological variables and deviation levels, participants were simply asked to make same/different judgments between pairs of stimuli rather than associate the sounds with specific physiologic variables. Participants were presented with the following instructions:

"You will now hear pairs of sounds. Your task is to determine whether they are the same or different. After you make your response, you will be given feedback as to whether your response was correct or incorrect."

Twenty-five trials were presented to each participant. On each trial, a pair of sounds was chosen from the library of sounds with the following constraints. Five of the trials contained identical sounds. In five of the trials the difference between sounds amounted to one "standard deviation" step along either of the two physiological variables. In five trials the difference amounted to two steps. This process was repeated for differences of 3 and 4 steps, resulting in an overall set of twenty-five trials. These were presented in random order to each participant. On each trial, a participant heard the pair of sounds once and then clicked "Same" or "Different" on the user interface. After the participant submitted their response, the word "Correct" or "Incorrect" appeared in green or red font, respectively, to provide feedback.

The objective of the "name-the-variable task" was to introduce meaning to the sounds. Participants were presented with the following instructions:

"You will now hear pairs of sounds. The second sound will always differ in one of two acoustical attributes. These attributes are intended to represent the physiological variables of oxygen saturation and heart rate. Your task is to name the variable that changed. You will be given feedback following each response. At first you may not know which acoustic attribute corresponds to which physiological variable so it is OK to guess. Use the feedback to learn which physiological variable goes with which acoustic attribute."

Pairs of sounds from the two-note discrimination task that differed were used for this task. In each trial, after hearing the pair of sounds, the participant was instructed to indicate whether the parameter was intended to denote a change to "Heart Rate" or "Oxygen Saturation." 8 trial types were repeated 3 times each. Four trial types represented changes in Heart Rate by one and two SDUs in either direction from the reference sound that was designated as the sound for the homeostatic state. Similarly, four trial types represented changes in Oxygen Saturation by one and two SDUs in either direction from the homeostatic state. Feedback was provided following each trial. Participants were not told ahead of time which acoustic attribute was intended to represent which parameter; they had to learn this based on the changes they heard and the feedback they received.

In the final task, the "change-magnitude" task, participants were asked to make judgments about changes in parameter magnitude, i.e. the number of "standard deviation" levels by which the two sounds differed. They were presented with the following instructions:

"You will now hear pairs of sounds. The second sound may be identical to the first sound, or one of its acoustical attributes may change. If the second sound differs from the first, it will do so by either a small amount or large amount. Your task is to indicate the amount of change—none, small, or large. You will be given feedback after you make your response. This is a difficult task, so don't worry if you get a lot of incorrect responses."

In any given trial, if the two sounds differed, it was only along one variable. After hearing a pair of sounds, subjects indicated whether the magnitude of the change was, "None," "Small," or "Large." There were nine trial types total, one representing no change, four representing a change of one standard deviation unit in either direction, and four representing a change of two standard deviation units in either direction. Each trial type was repeated five times for a total of 45 trials. In every trial the first sound represented z=0 along both acoustic dimensions. In other words, it served as a consistent reference point throughout this task. Participants were not explicitly asked to indicate which variable the change represented. Feedback on accuracy was provided after each trial.

After completing the three tasks participants answered a series of questions regarding their expectations coming into the testing session, their subjective assessment of the difficulty of the tasks, their performance, and the accessibility of the sonifications. An opportunity for open-ended comments was also provided.

Data were analyzed using custom MATLAB scripts. Statistical analyses were performed using routines from the Statistics Toolbox in MATLAB as well as SAS (SAS Institute, Inc.). The proportion of correct responses was calculated for each participant for each condition of interest and entered into a repeated-measures analysis of variance (ANOVA) in order to test for significant differences between conditions. Specific analyses are described in more detail in the Results section.

Results

On average, participants completed the experiment in 15.27 minutes (range: 11.43-21.57).

Two-Note Discrimination

Overall accuracy in the two-note discrimination task ranged between 84% and 100% with a mean of 94±1.1% (mean±s.e.m.). Fifteen of sixteen participants made no false alarms, and all participants performed perfectly when the difference between the two sounds spanned four SDUs. A 3-factor repeated-measures ANOVA was performed using PROC MIXED in SAS on the accuracy data from those conditions in which there was a difference between the two stimuli. The three factors were physiological dimension (2 levels: Oxygen Saturation, Heart Rate), SDU levels of change (4 levels: 1, 2, 3, 4), and direction of change (2 levels: down, up). As expected, there was a significant effect of change magnitude, $F(1,45)=16.03$; $p<0.0001$, with worst performance with only 1 SDU of change (76.25±4.17%) than for SDU levels 2-4 (97.5%, 97.5%, 100%, respectively). The effect of change direction was also significant, $F(1,15)=4.90$; $p<0.05$, as was the change magnitude by change direction interaction, $F(3,45)=6.16$; $p=0.0013$. The latter two effects were due to performance generally being better when there was an increase in the acoustic parameter, that is, a greater number of amplitude modulations (heart rate) or brightening of the timbre (oxygen saturation), with the exception of when the change was only 1 SDU, in which case downward changes were detected better. No other main effects or interactions were significant, including discrimination performance between the deviations occurring in the acoustic parameters intended to represent heart rate (93.75%) and oxygen saturation (91.41%). The strong performance in this task was reflected in participants' subjective assessment of task difficulty. When asked to endorse the statement, "How difficult did you find the task in which you had to indicate whether the sounds were the same or different?" 38% answered "somewhat easy," and 38% answered "very easy."

Name the Variable

Overall accuracy in the "name the variable" task ranged from 29.17% (1 participant) to 100% (3 participants) and averaged 73.70±5.93%, indicating that some individuals were immediately and consistently able to associate change in an acoustic parameter with the intended physiological variable, whereas some participants experienced considerable difficulty even after receiving feedback.

We performed a 3-factor repeated-measures ANOVA of the accuracy data, with physiological dimension (2 levels:

Oxygen Saturation, Heart Rate), SDU levels of change (2 levels: 1, 2), and direction of change (2 levels: down, up) as the three factors. There were no significant main effects or interactions in any of the factors. Participants were divided in their assessment of the difficulty of this task, with 50% answering that they found it somewhat or very difficult and 44% answering that they found it somewhat or very easy.

Change Magnitude

Average performance in the change magnitude task is shown in FIG. 15. Average overall accuracy was 66±3.6%, which was significantly above the chance performance level of 33% given the choices of "None," "Small," and "Large." Performance ranged from 46.67% to 97.78%, indicating that near perfect performance was possible given the variation in acoustic parameters. A 3-factor ANOVA was performed on the accuracy data from trials when a change was present, with physiological dimension (2 levels: Oxygen Saturation, Heart Rate), SDU levels of change (2 levels: 1, 2), and direction of change (2 levels: down, up) as the three factors. The main effect of physiological dimension was not significant [$F(1,15)=1.42$, n.s.], the main effect of SDU amount was not significant [$F(1,15)=1.15$, n.s.], and the main effect of direction of change was not significant [$F(1,15)=1.15$, n.s.]. Of the interactions, only the SDU level of change× direction of change was significant [$F(1, 15)=8.86$; $p<0.01$], and was due to better detection of downward changes of 1 SDU but better detection of upward changes of 2 SDUs. The subjects considered this to be the most difficult task, as was reflected in the subjective assessments. No subject indicated that the task was very easy, and 75% responded that they found it somewhat or very difficult.

Overall performance across the three tasks decreased as anticipated. While most participants were able to discriminate between the different sounds quite well, assuming the difference between them encompassed at least 2 SDU levels, the requirements of associating a meaning with the sounds or determining the precise amount of change resulted in worse performance. Interestingly, the propensity to indicate that a change occurred when actually none had occurred (false alarms) in the change-magnitude task was higher than when a simple yes/no difference judgment was required in the two-note discrimination task.

It is perceived that with additional training, most of the participants could learn to associate the sounds with the intended SDU levels along both of the acoustical dimensions. When asked to endorse the statement, "With additional practice, I would be able to detect changes in the sounds more easily," 44% of the participants answered "Somewhat agree" and 31% answered "Strongly agree." When asked to estimate how much more training they might require, 25% felt that 30 minutes would suffice, 19% that 2 hours would suffice, and 44% felt that 5-10 work days of hearing the sounds used in real-life situations would be adequate. This optimism that the sounds could be learned in such a short time extended to the belief that clinically-relevant monitoring would be feasible with sonifications designed upon the basic principles embodied in this experiment. When given the statement, "I am confident that with more practice I would be able to tell what is happening with a patient over time just by listening to sounds like these, even if not these exact sounds," 75% of the participants voiced moderate to strong agreement. Overall, the experiment boosted individuals' confidence in their ability to tell sounds apart based on subtle differences in 44% of the participants, but decreased the confidence in 31% of the participants.

Experiment 2

This experiment served to replicate and extend the initial experiment. First, it measured the implicit interpretability of the sonification method by measuring initial performance without feedback in each of the conditions in Experiment 1. Second, it sought to determine whether an increase in the amount of training (up to 90 minutes) for participants who required it would lead to better performance on the name the variable and change magnitude tasks. We regarded the limit of 90 minutes as a reasonable criterion for assessing whether the sonification strategy would meet the goal of easy learnability.

17 staff members (16 female) aged 24-55 years (mean±std: 44.1±10.2) from the ICN at CHaD participated in the experiment. Two participants had participated in Experiment 1 and were excluded from the analyses reported below.

The stimuli were identical to those used in Experiment 1.

The sequence of tasks was the same as in Experiment 1 with a small number of modifications. The number of no-change trials in the two-note discrimination task was doubled, resulting in 30 trials total. A substantive change was that performance was assessed without feedback during the initial 27 trials in the name the variable and change magnitude tasks. Following both the name the variable and change magnitude tasks, additional trials with feedback (training trials) were repeated until the participant either reached the running average performance criterion of 87.5% correct (21 of the last 24 trials) or the total assessment and training time exceeded 90 minutes. Performance during the assessment trials was taken into account when computing the running performance criterion. It was therefore possible for a participant to complete only a single training trial before continuing to the next phase of the experiment. The final performance data in the name the variable and change magnitude tasks comprised the last three trials completed in each of the eight condition combinations across the three factors that were varied (physiological dimension, SDU level of change, direction of change), e.g., 1 SDU change downward for heart rate.

Results

Two-Note Discrimination

Overall accuracy in the two-note discrimination task ranged from 60% to 100% with a mean of 92.22±2.36% (mean±s.e.m.). Thirteen of 15 participants made no false alarms, and 12 of 15 participants performed perfectly when the difference between the two sounds spanned four SDUs. A 3-factor repeated-measures ANOVA, with physiological dimension (2 levels: Oxygen Saturation, Heart Rate), SDU levels of change (4 levels: 1, 2, 3, 4), and direction of change (2 levels: down, up) as the three factors showed a significant difference in accuracy across the four levels of SDUs [$F(3,42)=7.84$; $p=0.0003$]. This effect was due to lower accuracy (74.86±3.55%) when the amount of change was only 1 SDU compared to 2-4 SDUs (mean accuracies: 93.06%, 95.54%, 96.68%, respectively). No other main effects or interactions were significant.

Name the Variable

During the assessment phase (without feedback), overall accuracy in the "name the variable" task ranged from 16.8% to 100% and averaged 73.33%. The mean accuracies for the oxygen saturation (71.67%) and heart rate (75.00%) parameters were not significantly different [$t(14)=0.364$, n.s.].

Forty percent of the participants reached criterion performance (87.5%) during the assessment and needed no training. The number of training trials ranged from 2-217 (M=72, SD=75). Training times ranged from 6.3 to 59.4 minutes (M=23.8 min). All but two participants who received training reached criterion. One participant trained for ~37 min, achieved 50% accuracy and withdrew from the experiment. The other reached 83.3% accuracy after 59.4 minutes of training and withdrew the experiment in order to return to work duties.

Separate 3-factor repeated measures ANOVA with physiological dimension (2 levels: Oxygen Saturation, Heart Rate), SDU levels of change (2 levels: 1, 2), and direction of change (2 levels: down, up) as the three factors, were performed for the assessment data (obtained feedback), and the final performance data. There were no significant main effects or interactions in the assessment data. In the final performance data, a significant main effect of physiological dimension was observed, with significantly better labeling of changes in oxygen saturation (92.22±2.96%) than heart rate (79.44±2.96%). Additionally, a main effect of direction of change indicated worse labeling of the physiological dimension when the change was downward (81.11±2.96%) than when it was upward (90.56±2.96%).

Change Magnitude

During initial assessment without feedback, average accuracy was 71.79±5.23% (range: 22.2-96.3%), which was significantly above the chance performance level of 33%. FIG. 16 illustrates the accuracy data as a function of the three factors, both before and after training. A 3-factor ANOVA of the data from no-feedback trials before training when a change was present showed no significant main effects. Three interactions were significant. The interaction between physiological dimension and magnitude of change was significant [$F(1,12)=7.27$, $p=0.0195$.], and arose from the fact that while a large change in heart rate was discerned better than a small change in heart rate, the opposite was true for oxygen saturation. A significant interaction of physiological dimension and direction of change [$F(1,12)=5.27$; $p<0.05$] arose from much better identification of downward changes in heart rate relative to upward changes, whereas the detection of downward changes on oxygen saturation tended to be as accurate or slightly worse than upward changes. The direction and magnitude of change also interacted significantly [$F(1,12)=12.21$; $p=0.0044$], and arose from large upward changes and small downward changes being identified better than small upward and large downward changes. The 3-way interaction was not significant.

FIG. 16 illustrates that training improved performance (by definition). A 3-factor ANOVA was performed as for the assessment phase. The pattern of results was the same, except that the physiological dimension×magnitude of change interaction was no longer significant. The physiological dimension×direction of change interaction remained significant [$F(1,12)=18.75$; $p=0.001$], with downward changes identified better in the case of heart rate and upward changes identified better for oxygen saturation. The direction and magnitude of change also interacted significantly [$F(1,12)=10.55$; $p=0.007$], with the same interaction pattern as described above. Overall, those discriminations that were difficult during the assessment phase continued to be more difficult following training. Nonetheless, the limited training regime within this experiment appeared to be successful.

We examined the counterintuitive finding that large changes in oxygen saturation were more difficult to detect than small changes in oxygen saturation (FIG. 16) in more detail, by comparing response accuracy for changes in each direction. We found that changes in the direction of higher oxygen saturation were detected with 92.3% accuracy following training, whereas downward changes were identified correctly only 53.8% of the time. This result was somewhat surprising, as both the small changes and the large upward change were more similar to each other in terms of variation in the amount of shimmer imparted on the carrier frequency than they were to the sound representing a large downward change. The latter represented a desaturated state with an almost pure flute-like sound. We believe this result may be due to semantic confusion in the sense that the flute-like timbre is less rich than the other oxygen timbres and sounds feebler and more compact, and in that sense small. Thus, when having to match on each trial the sense of change in timbre of the sound with the labels, None, Small, and Large, the "small" sound of the large downward change in implied oxygen saturation could easily be mis-categorized. Indeed, all of the errors were of this type. Further instructions to the participants discussing this possible confusion, or adding at least a small amount of shimmer to the highly desaturated sound may help improve categorization of large downward changes. Two participants required no training. Of the 13 who required training, 11 reached criterion within the allotted time. Note that the performance criterion was overall accuracy in the task rather than accuracy within each combination of physiological parameter and change magnitude. Thus, a participant could have correctly detected no change in all cases, but small changes in oxygen saturation only 70% of the time. The average number of trials to reach criterion was 66±46 (range: 5-146) with an average training time of 19.8±11.2 min (range: 4.8-43 min).

Overall, the responses on the post-experiment questionnaire echoed those from Experiment 1. The experienced difficulty progressed across the three conditions. Nonetheless, participants were positive and optimistic with regard to their potential for improvement and the utility of similar sonifications in their workplace environment. Seventy-four percent agreed somewhat or strongly that having completed the experiment they felt more confident in their ability to tell apart sounds based on subtle differences, and 86% believed that with additional practice they would be able to detect changes in the sounds more easily. All of those who completed the experiment were confident that with more practice they would be able to ascertain patient vitals status over time just by listening to sounds like these (80% somewhat agree; 20% strongly agree).

The results of Experiment 2 confirmed and extended the results of Experiment 1. Mean accuracies in the assessment phases of all three conditions were very similar to those of Experiment 1. This indicated that even though participants were not receiving feedback, they were able to understand the intent of the sonifications as accurately as when exposed to the sonification strategy for the first time with feedback. With additional training, all participants improved in their performance and over 87% achieved the required performance criterion within the 90 minutes allowed for the session, indicating that the basic principles of the sonification strategy could be learned within a fairly short amount of time. Discrimination of change magnitudes was easier for heart rate, likely because the number of amplitude modulations (1-5) could be counted.

Although retention of the sonifications was not tested, due to clinical demands on participants' time, one participant actually completed Experiment 2 twice, with the testing sessions 7 weeks apart (only the data from the first session were used in the analyses presented above). During the first session, the participant required a total of 50 trials on the "name the variable" task to perform with 84% accuracy and 120 trials (~20 minutes of training) on the "change magnitude" task to perform with 76% overall accuracy. 7 weeks later, the participant scored 100% and 82% in the assessment phases of the "name the variable" and "change magnitude" tasks, respectively, indicating excellent retention of the sonification method.

The goal of this study was to evaluate the ability of clinical practitioners to discriminate and categorize sounds intended to convey changes in oxygen saturation and heart rate. The sounds simultaneously communicated information about the two physiological variables: an amplitude modulation cue was used to signal changes in heart rate, and a timbral cue was used to signal changes in oxygen saturation.

The perfect or near-perfect performance of a number of individuals across all of the tasks established that the range of acoustic variation could be mapped onto the intended range of physiological variable variation and associated with the intended meanings with relatively little effort or training. In other words, the acoustic dimensions had the property of auditory icons, at least in the context of a forced-choice categorization of a varying acoustic dimension. In the majority of participants, however, the iconic aspects of the sounds had to be reinforced with a modest amount of training, whereafter almost all individuals could reliably associate an acoustic cue with a physiological variable and discriminate different levels of variation along that variable. A small number of individuals had difficulty with the tasks, even after training, likely leading to their withdrawal from the study.

Variation in auditory discrimination abilities is expected in a normal population. For example, a small percentage of the population suffers from amusia—an impairment in the ability to determine the direction of pitch changes, and the acuity with which people are able to discriminate or maintain in memory representations of the pitch of single notes varies widely in young adults and correlates with the amount of musical training. Musical training was not assessed in this particular sample, and while it may influence the degree to which any given individual is able to make use of a sonification strategy, the point remains that decision-making based on acoustic cues is unlikely to be reliable for some individuals. Moreover, it may be advisable to obtain audiometric profiles and information about musical background from participants in future.

Basic discrimination performance suggested that the amount of acoustic variation should be increased slightly in order to attain perfect discrimination performance at all levels of deviation. For example, the dissonant qualities of the sound that denote extremely high oxygen saturation could be accentuated by increasing the harmonicity ratio (the ratio of the modulation and carrier frequencies) or by changing the harmonicity ratio through time. These manipulations would likely make the sound even more alarming and urgent and more easily discriminable from the oxygen saturation levels denoting $z=0$ and $z=+1$.

Implications for Principles of Sonification Design

The assumption underlying the sonification methods deployed in these experiments is that a small set of mappings between physiological deviation levels and acoustic changes should be easier to learn and utilize than a continuous mapping between absolute values of physiologic and acoustic variables. The greater difficulty experienced when making change magnitude judgments would appear to support this assumption. Although the same magnitudes of change were easily detected when the task was simply to report change, it was the added cognitive step of assigning meaning to the specific change that posed the challenge. Thus, restricting the number of meaningful steps in the sonification should eliminate the need for continually evaluating whether the magnitude of change in the absolute value of a parameter over some amount of time is clinically meaningful.

The sonification method of the technology described herein differs from existing systems that operate on an assumption that continuous auditory displays, such as existing pulse oximeters, are preferable because they support continuous awareness, and therefore the possibility of immediate detection of a significant change. Two senses of the word "continuous" are relevant here. One is continuous variation along a physiological dimension that is mapped to continuous variation along an acoustic dimension, e.g., the mapping of oxygen saturation to pitch. The other is continuity in time, i.e. how frequently the information is made available to the perceiver. The sonification method of the technology described herein discretizes the auditory information both in acoustic and temporal dimensions to reduce the perceptual and cognitive demands of monitoring the sonification.

An additional benefit to restricting the sounds to a small number of categories is that once these mappings are learned, the actual cutoff points that separate the five levels of acoustic variation for any given physiological variable could be set at clinically meaningful levels and still retain their signaling utility. Although we refer to them as standard deviation units (SDUs) in the present study, the ability to set two arbitrary transition points on either side of the target, homeostatic, value is particularly important in scenarios in which the moderately and highly critical values of a particular physiological variable, e.g., oxygen saturation, are not positioned at equal distances on a normal distribution around a designated target value. Moreover, if the desired target value changes as a function of time during a specific clinical scenario, such as delivery room stabilization, the transition points at which the sonification changes could be set dynamically. Thus, the discrete levels of the sonification come to signify relative states of well-being rather than continuously varying absolute values of physiological parameters.

A further important aspect of this sonification method is that the information about whether the current state differs from a target state is encapsulated into a sonification item lasting 1.75 seconds. The target state is sonically generated first followed immediately by the current state. Thus, the practitioner need not compare the momentary state against a target state (absolute value of an acoustic parameter) maintained in long-term memory. Moreover, these information packets can be presented at arbitrary desired rates, e.g., every 3 seconds or every 10 seconds, to meet the requirements of the specific situation. These reduced presentation rates, compared with the existing pulse oximeter sonification, should reduce the overall amount of "auditory clutter" in the environment. Experiments would need to determine whether such reductions would translate to reduced stress levels, both in patients and clinicians.

The systems and methods of the technology described herein provide an effective method for presenting information about physiological parameters such as oxygen saturation and heart rate parameters in discrete auditory events. In a preferred embodiment, each event comprises of two sounds. The first is a reference sound that indicates the desired target state for the two parameters and the second indicates the actual state. Heart rate is preferably represented by amplitude modulation, with one cycle per event connoting very low heart rate, and five cycles per event connoting very high heart rate. Oxygen saturation is preferably represented by a timbral manipulation that varies the sound from a pure tone (connoting low oxygen saturation) through one containing a significant amount of shimmer (connoting high oxygen saturation).

Variation in each parameter is preferably restricted to five discrete tonal characteristics, two representing abnormally low states relative to the target state and two representing abnormally high states. For example, these five discrete tonal characteristics for the actual state sounds can be used to denote discrete actual state categories such as (1) critically low, (2) moderately low, (3) target, (4) moderately high, and (5) critically high.

This approach represents a major improvement over current sonification approaches in which variation in the acoustic parameters is continuous and tied to absolute values of those parameters and which, therefore, are more difficult to understand. In the discussion above, these five categories are described in terms of standard deviation units (SDUs). In statistics, parameter values can be expressed as z-scores which are standardized data values such that $z=1$ represents a value one standard deviation away from the mean value. Here, the mean value would be interpreted as the desired target state and would have a value of $z=0$. The five applicable values are: $z<=-2$, $-2<z<=-1$, $-1<z<1$, $1<=z<2$, $z>=2$. While z-scores are typically used to refer to values from a normal distribution, and are easily understood as such, the technology described herein is broader in recognition of the fact that the physiological parameter values of interest are not necessarily distributed normally. Thus, the broader construal of the five categories and their boundaries can be thought of in terms of "event criticality", with values corresponding to $z=-1$ and $z=1$ to be interpreted as "warnings" and values $z=-2$ and $z=2$ to be interpreted as "critical" events. The actual set-points of these boundaries depend on the specific clinical scenario.

The mapping between actual physiological parameter values and crossings from one state to another is flexible and can be set based on the needs of the specific clinical scenario. The auditory (sonification) events occur at regular intervals, e.g., 2 seconds to 10 seconds, that can be set as desired. Thus, this sonification provides a "continuous" information stream about a combination of physiological parameters, in this case heart rate and oxygen saturation, without being as obtrusive as current pulse oximeter sonification strategies, e.g., pitch that varies with each heartbeat.

From the description herein it will be appreciated the technology described herein can be implemented in various embodiments which include but are not limited to the following:

1. A system for generating a sonification output for data relating to one or more physiological parameters, the system comprising: a processor; programming executable on the processor for: (a) receiving data relating to one or more physiological parameters; (b) comparing the received data to a plurality of thresholds correlating to discrete events with respect to the one or more physiological parameters; (c) said plurality of thresholds comprising a first upper threshold and first lower threshold defining bounds for a target state within the data for each of the one or more physiological parameters; (d) said plurality of thresholds comprising a second upper threshold and second lower threshold with respect to the target state within the data for each of the one or more physiological parameters; (e) wherein data falling within the first upper threshold and second upper threshold represents a first upper warning state, data falling within the first lower threshold and second lower threshold represents a first lower warning state; data falling above the second upper threshold represents a second upper warning state, and data falling below the second lower threshold represents a second lower warning state; (f) generating a sonification output based on the value of the data and the plurality of thresholds; and (g) wherein the sonification output comprises five discrete and discernible audible signals representing data values within the target state, first upper warning state, second upper warning state, first lower warning state, and second lower warning state.

2. The system of any of the previous embodiments: wherein the one or more physiological parameters comprise at least two physiological parameters; and wherein the sonification output is comprises a distinct audible output for each of the physiological parameters.

3. A system as in any of the proceeding embodiments, wherein generating the sonification output comprises: generating first and second audible sounds; first sound comprising a reference sound corresponding to the target state; said second sound corresponding to corresponding to an actual state.

4. The system of any of the previous embodiments, wherein the first and second sounds are modified by one or more auditory parameters consisting one or more of duration, frequency, amplitude, shimmer and modulation rate.

5. The system of any of the previous embodiments, wherein the one or more physiological parameters comprise oxygen saturation and heart rate.

6. The system of any of the previous embodiments: wherein heart rate is represented in said first and second sounds by amplitude modulation; and wherein oxygen saturation is represented in said first and second sounds by frequency modulation.

7. The system of any of the previous embodiments, wherein oxygen saturation is represented in said first and second sounds by timbral manipulation of the sounds.

8. The system of any of the previous embodiments, wherein oxygen saturation is represented in said first and second sounds by timbral manipulation of the sounds that varies the sound from a first pure tone to a second tone containing shimmer.

9. The system of any of the previous embodiments, wherein the first tone denotes oxygen saturation below target and the second tone denotes oxygen saturation above target.

10. The system of any of the previous embodiments, wherein the amplitude modulation is varied between a first number of cycles per event denoting a heart rate below the target state and a second number of cycles per event denoting a heart rate above the target state.

11. The system of any of the previous embodiments, wherein one or more of the plurality of thresholds dynamically vary over time.

12. A method for generating a sonification output for data relating to one or more physiological parameters, the method comprising: receiving data relating to one or more physiological parameters; comparing the received data to a plurality of thresholds correlating to discrete events with respect to the one or more physiological parameters; said plurality of thresholds comprising a first upper threshold and first lower threshold defining bounds for a target state within the data for each of the one or more physiological parameters; said plurality of thresholds comprising a second upper threshold and second lower threshold with respect to the target state within the data for each of the one or more physiological parameters; wherein data falling within the first upper threshold and second upper threshold represents a first upper warning state, data falling within the first lower threshold and second lower threshold represents a first lower warning state; data falling above the second upper threshold represents a second upper warning state, and data falling below the second lower threshold represents a second lower warning state; generating a sonification output based on the value of the data and the plurality of thresholds; and wherein the sonification output comprises five discrete and discernible audible signals representing data values within the target state, first upper warning state, second upper warning state, first lower warning state, and second lower warning state.

13. The method of any of the previous embodiments: wherein the one or more physiological parameters comprise at least two physiological parameters; and wherein the sonification output is comprises a distinct audible output for each of the physiological parameters.

14. The method of any of the previous embodiments, wherein generating the sonification output comprises: generating first and second audible sounds; first sound comprising a reference sound corresponding to the target state; said second sound corresponding to corresponding to an actual state.

15. The method of any of the previous embodiments, wherein the first and second sounds are modified by one or more auditory parameters consisting one or more of duration, frequency, amplitude, shimmer and modulation rate.

16. The method of any of the previous embodiments, wherein the one or more physiological parameters comprise oxygen saturation and heart rate.

17. The method of any of the previous embodiments: wherein heart rate is represented in said first and second sounds by amplitude modulation; and wherein oxygen saturation is represented in said first and second sounds by frequency modulation.

18. The method of any of the previous embodiments, wherein oxygen saturation is represented in said first and second sounds by timbral manipulation of the sounds.

19. The method of any of the previous embodiments, wherein oxygen saturation is represented in said first and second sounds by timbral manipulation of the sounds that varies the sound from a first pure tone to a second tone containing shimmer.

20. The method of any of the previous embodiments, wherein the first tone denotes oxygen saturation below target and the second tone denotes oxygen saturation above target 21. The method of any of the previous embodiments, wherein the amplitude modulation is varied between a first number of cycles per event denoting a heart rate below the target state and a second number of cycles per event denoting a heart rate above the target state.

22. A system for monitoring data relating to one or more physiological parameters, the system comprising: one or more sensors for acquiring data relating to one or more physiological parameters; a processor; a speaker coupled to the processor; programming executable on the processor for: (a) receiving data relating to one or more physiological parameters; (b) comparing the received data to a plurality of thresholds correlating to discrete events with respect to the one or more physiological parameters; (c) said plurality of thresholds comprising a first upper threshold and first lower threshold defining bounds for a target state within the data for each of the one or more physiological parameters; (d) said plurality of thresholds comprising a second upper threshold and second lower threshold with respect to the target state within the data for each of the one or more physiological parameters; (e) wherein data falling within the first upper threshold and second upper threshold represents a first upper warning state, data falling within the first lower threshold and second lower threshold represents a first lower warning state; data falling above the second upper threshold represents a second upper warning state, and data falling below the second lower threshold represents a second lower warning state; (f) generating an audio file for playback on said speaker based on the value of the data and the plurality of thresholds; and (g) wherein the audio file comprises five discrete and discernible audible signals representing data values within the target state, first upper warning state, second upper warning state, first lower warning state, and second lower warning state.

23. The system of any of the previous embodiments: wherein the one or more physiological parameters comprise at least two physiological parameters; and wherein the sonification output is comprises a distinct audible output for each of the physiological parameters.

24. The system of any of the previous embodiments, wherein generating the audio file comprises: generating first and second audible sounds; first sound comprising a reference sound corresponding to the target state; said second sound corresponding to corresponding to an actual state.

25. The system of any of the previous embodiments, wherein the first and second sounds are modified by one or more auditory parameters consisting one or more of duration, frequency, amplitude, shimmer and modulation rate.

26. The system of any of the previous embodiments, wherein the one or more physiological parameters comprise oxygen saturation and heart rate.

27. The system of any of the previous embodiments: wherein heart rate is represented in said first and second sounds by amplitude modulation; and wherein oxygen saturation is represented in said first and second sounds by frequency modulation.

28. The system of any of the previous embodiments: wherein oxygen saturation is represented in said first and second sounds by timbral manipulation of the sounds that varies the sound from a first pure tone to a second tone containing shimmer; and wherein the first tone denotes oxygen saturation below target and the second tone denotes oxygen saturation above target 29. The system of any of the previous embodiments, wherein the amplitude modulation is varied between a first number of cycles per event denoting a heart rate below the target state and a second number of cycles per event denoting a heart rate above the target state.

30. A method for monitoring oxygen saturation and heart rate parameters in discrete auditory events, the method comprising: (a) generating first and second audible sounds; (b) said first sound comprising a reference sound corresponding to a desired target state; (c) said second sound corresponding to an actual state; (d) wherein heart rate is represented in said first and second sounds by amplitude modulation; (e) wherein oxygen saturation is represented in said sounds by timbral variation; and (f) wherein deviation from said second sound with said first sound represents an audible cue of a deviation in said actual state from said target state.

Embodiments of the technology described herein may be described with reference to flowchart illustrations of methods and systems according to embodiments of the technology, and/or algorithms, formulae, or other computational depictions, which may also be implemented as computer program products. In this regard, each block or step of a flowchart, and combinations of blocks (and/or steps) in a flowchart, algorithm, formula, or computational depiction can be implemented by various means, such as hardware, firmware, and/or software including one or more computer program instructions embodied in computer-readable program code logic. As will be appreciated, any such computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s).

Accordingly, blocks of the flowcharts, algorithms, formulae, or computational depictions support combinations of means for performing the specified functions, combinations of steps for performing the specified functions, and computer program instructions, such as embodied in computer-readable program code logic means, for performing the specified functions. It will also be understood that each block of the flowchart illustrations, algorithms, formulae, or computational depictions and combinations thereof described herein, can be implemented by special purpose hardware-based computer systems which perform the specified functions or steps, or combinations of special purpose hardware and computer-readable program code logic means.

Furthermore, these computer program instructions, such as embodied in computer-readable program code logic, may also be stored in a computer-readable memory that can direct a computer or other programmable processing apparatus to function in a particular manner, such that the instructions stored in the computer-readable memory produce an article of manufacture including instruction means which implement the function specified in the block(s) of the flowchart(s). The computer program instructions may also be loaded onto a computer or other programmable processing apparatus to cause a series of operational steps to be performed on the computer or other programmable processing apparatus to produce a computer-implemented process such that the instructions which execute on the computer or other programmable processing apparatus provide steps for implementing the functions specified in the block(s) of the flowchart(s), algorithm(s), formula(e), or computational depiction(s).

It will further be appreciated that the terms "programming" or "program executable" as used herein refer to one or more instructions that can be executed by a processor to perform a function as described herein. The instructions can be embodied in software, in firmware, or in a combination of software and firmware. The instructions can be stored local to the device in non-transitory media, or can be stored remotely such as on a server, or all or a portion of the instructions can be stored locally and remotely. Instructions stored remotely can be downloaded (pushed) to the device by user initiation, or automatically based on one or more factors. It will further be appreciated that as used herein, that the terms processor, computer processor, central processing unit (CPU), and computer are used synonymously to denote a device capable of executing the instructions and communicating with input/output interfaces and/or peripheral devices.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. A system for generating a sonification output for data relating to one or more physiological parameters, the system comprising:
    a processor;
    programming executable on the processor for:
        (a) receiving data relating to one or more physiological parameters;
        (b) comparing the received data to a plurality of thresholds correlating to discrete events with respect to the one or more physiological parameters;
        (c) said plurality of thresholds comprising a first upper threshold and first lower threshold defining bounds for a target state within the data for each of the one or more physiological parameters;
        (d) said plurality of thresholds comprising a second upper threshold and second lower threshold with respect to the target state within the data for each of the one or more physiological parameters;
        (e) wherein data falling within the first upper threshold and second upper threshold represents a first upper warning state, data falling within the first lower threshold and second lower threshold represents a first lower warning state; data falling above the second upper threshold represents a second upper warning state, and data falling below the second lower threshold represents a second lower warning state;
        (f) generating a sonification output based on the value of the data and the plurality of thresholds; and
        (g) wherein the sonification output comprises five discrete and discernible audible signals representing data values within the target state, first upper warning state, second upper warning state, first lower warning state, and second lower warning state.

2. A system as recited in claim 1:
    wherein the one or more physiological parameters comprise at least two physiological parameters; and
    wherein the sonification output is comprises a distinct audible output for each of the physiological parameters.

3. A system as recited in claim 2, wherein generating the sonification output comprises:
    generating first and second audible sounds;
    said first sound comprising a reference sound corresponding to the target state;
    said second sound corresponding to an actual state.

4. A system as recited in claim 3, wherein the first and second sounds are modified by one or more auditory parameters consisting one or more of duration, frequency, amplitude, shimmer and modulation rate.

5. A system as recited in claim 4:
    wherein heart rate is represented in said first and second sounds by amplitude modulation; and wherein oxygen saturation is represented in said first and second sounds by frequency modulation.

6. A system as recited in claim 5, wherein oxygen saturation is represented in said first and second sounds by timbral manipulation of the sounds.

7. A system as recited in claim 6, wherein the timbral manipulation varies the sound from a first pure tone to a second tone containing shimmer.

8. A system as recited in claim 7, wherein the first tone denotes oxygen saturation below target and the second tone denotes oxygen saturation above target.

9. A system as recited in claim 3, wherein the one or more physiological parameters comprise oxygen saturation and heart rate.

10. A system as recited in claim 5, wherein the amplitude modulation is varied between a first number of cycles per event denoting a heart rate below the target state and a second number of cycles per event denoting a heart rate above the target state.

11. A system as recited in claim 1, wherein one or more of the plurality of thresholds dynamically vary over time.

12. A method for generating a sonification output for data relating to one or more physiological parameters, the method comprising:
receiving data relating to one or more physiological parameters;
comparing the received data to a plurality of thresholds correlating to discrete events with respect to the one or more physiological parameters;
said plurality of thresholds comprising a first upper threshold and first lower threshold defining bounds for a target state within the data for each of the one or more physiological parameters;
said plurality of thresholds comprising a second upper threshold and second lower threshold with respect to the target state within the data for each of the one or more physiological parameters;
wherein data falling within the first upper threshold and second upper threshold represents a first upper warning state, data falling within the first lower threshold and second lower threshold represents a first lower warning state; data falling above the second upper threshold represents a second upper warning state, and data falling below the second lower threshold represents a second lower warning state;
generating a sonification output based on the value of the data and the plurality of thresholds; and
wherein the sonification output comprises five discrete and discernible audible signals representing data values within the target state, first upper warning state, second upper warning state, first lower warning state, and second lower warning state.

13. A method as recited in claim 12:
wherein the one or more physiological parameters comprise at least two physiological parameters; and
wherein the sonification output is comprises a distinct audible output for each of the physiological parameters.

14. A method as recited in claim 13, wherein generating the sonification output comprises:
generating first and second audible sounds;
said first sound comprising a reference sound corresponding to the target state;
said second sound corresponding to an actual state.

15. A method as recited in claim 14, wherein the first and second sounds are modified by one or more auditory parameters consisting one or more of duration, frequency, amplitude, shimmer and modulation rate.

16. A method as recited in claim 14, wherein the one or more physiological parameters comprise oxygen saturation and heart rate.

17. A method as recited in claim 16:
wherein heart rate is represented in said first and second sounds by amplitude modulation; and
wherein oxygen saturation is represented in said first and second sounds by frequency modulation.

18. A method as recited in claim 17, wherein oxygen saturation is represented in said first and second sounds by timbral manipulation of the sounds.

19. A method as recited in claim 18, wherein the timbral manipulation varies the sound from a first pure tone to a second tone containing shimmer.

20. A method as recited in claim 19, wherein the first tone denotes oxygen saturation below target and the second tone denotes oxygen saturation above target.

21. A method as recited in claim 17, wherein the amplitude modulation is varied between a first number of cycles per event denoting a heart rate below the target state and a second number of cycles per event denoting a heart rate above the target state.

22. A system for monitoring data relating to one or more physiological parameters, the system comprising:
one or more sensors for acquiring data relating to one or more physiological parameters;
a processor;
a speaker coupled to the processor;
programming executable on the processor for:
(a) receiving data relating to one or more physiological parameters;
(b) comparing the received data to a plurality of thresholds correlating to discrete events with respect to the one or more physiological parameters;
(c) said plurality of thresholds comprising a first upper threshold and first lower threshold defining bounds for a target state within the data for each of the one or more physiological parameters;
(d) said plurality of thresholds comprising a second upper threshold and second lower threshold with respect to the target state within the data for each of the one or more physiological parameters;
(e) wherein data falling within the first upper threshold and second upper threshold represents a first upper warning state, data falling within the first lower threshold and second lower threshold represents a first lower warning state; data falling above the second upper threshold represents a second upper warning state, and data falling below the second lower threshold represents a second lower warning state;
(f) generating an audio file for playback on said speaker based on the value of the data and the plurality of thresholds; and
(g) wherein the audio file comprises five discrete and discernible audible signals representing data values within the target state, first upper warning state, second upper warning state, first lower warning state, and second lower warning state.

23. A system as recited in claim 22:
wherein the one or more physiological parameters comprise at least two physiological parameters; and
wherein the sonification output is comprises a distinct audible output for each of the physiological parameters.

24. A system as recited in claim 23, wherein generating the audio file comprises:

generating first and second audible sounds;
said first sound comprising a reference sound corresponding to the target state;
said second sound corresponding to corresponding to an actual state.

25. A system as recited in claim 24, wherein the first and second sounds are modified by one or more auditory parameters consisting one or more of duration, frequency, amplitude, shimmer and modulation rate.

26. A system as recited in claim 24, wherein the one or more physiological parameters comprise oxygen saturation and heart rate.

27. A system as recited in claim 26:
wherein heart rate is represented in said first and second sounds by amplitude modulation; and
wherein oxygen saturation is represented in said first and second sounds by frequency modulation.

28. A system as recited in claim 27:
wherein oxygen saturation is represented in said first and second sounds by timbral manipulation of the sounds that varies the sound from a first pure tone to a second tone containing shimmer; and
wherein the first tone denotes oxygen saturation below target and the second tone denotes oxygen saturation above target.

29. A system as recited in claim 27, wherein the amplitude modulation is varied between a first number of cycles per event denoting a heart rate below the target state and a second number of cycles per event denoting a heart rate above the target state.

30. A method for monitoring oxygen saturation and heart rate parameters in discrete auditory events, the method comprising:
(a) generating first and second audible sounds;
(b) said first sound comprising a reference sound corresponding to a desired target state;
(c) said second sound corresponding to an actual state;
(d) wherein heart rate is represented in said first and second sounds by amplitude modulation;
(e) wherein oxygen saturation is represented in said sounds by timbral variation; and
(f) wherein deviation from said second sound with said first sound represents an audible cue of a deviation in said actual state from target state.

* * * * *